United States Patent
Huang

(10) Patent No.: US 9,346,833 B2
(45) Date of Patent: May 24, 2016

(54) TRIFLUOROBORATE MASS SPECTROMETRIC TAGS

(71) Applicant: CellMosaic, Inc., Worcester, MA (US)

(72) Inventor: Yumei Huang, Lexington, MA (US)

(73) Assignee: CellMosaic, Inc., Woburn, MA (US)

( * ) Notice: Subject to any disclaimer, the term of this patent is extended or adjusted under 35 U.S.C. 154(b) by 0 days.

(21) Appl. No.: 14/779,805

(22) PCT Filed: Mar. 26, 2014

(86) PCT No.: PCT/US2014/031795
§ 371 (c)(1),
(2) Date: Sep. 24, 2015

(87) PCT Pub. No.: WO2014/160739
PCT Pub. Date: Oct. 2, 2014

(65) Prior Publication Data
US 2016/0052942 A1    Feb. 25, 2016

Related U.S. Application Data

(60) Provisional application No. 61/805,644, filed on Mar. 27, 2013.

(51) Int. Cl.
*H01J 49/40*     (2006.01)
*C07F 5/02*      (2006.01)
*C08G 65/34*     (2006.01)
*H01J 49/00*     (2006.01)

(52) U.S. Cl.
CPC . *C07F 5/02* (2013.01); *C07F 5/025* (2013.01); *C08G 65/34* (2013.01); *H01J 49/0027* (2013.01)

(58) Field of Classification Search
CPC .. C07D 401/14; C07D 401/04; C07D 403/04; C07D 403/14; C07D 405/04; C07D 413/14; C07D 417/14; C07D 5/02; H01J 49/0027
USPC .......... 250/281, 282; 514/210.18, 230.2, 248, 514/252.05, 269, 341, 406; 544/101, 235
See application file for complete search history.

(56) References Cited

U.S. PATENT DOCUMENTS

| | | | |
|---|---|---|---|
| 9,090,586 B2 * | 7/2015 | Yoshikawa | C07D 401/14 514/211.15 |
| 2013/0137675 A1 * | 5/2013 | Taniguchi | C07D 401/04 514/210.18 |
| 2014/0220573 A1 * | 8/2014 | Hrdlicka | C07H 19/06 435/6.11 |
| 2016/0052942 A1 * | 2/2016 | Huang | C07F 5/02 250/282 |

OTHER PUBLICATIONS

Petrillo et al., Accurate Mass Determination of Organotrifluoroborates, Nov. 16, 2006, Journal of the American Society for Mass Spectometry, 18, 404-405.*

* cited by examiner

*Primary Examiner* — David A Vanore
(74) *Attorney, Agent, or Firm* — Milstein Zhang & Wu LLC

(57) ABSTRACT

The invention provides compositions and methods for mass spectrometric (MS), organic synthesis, and applications of organo-trifluoroborate, for example, as mass tags for use in negative ion mode. When subject to MS fragmentation, organo-trifluoroborates preferentially undergo neutral losses of hydrogen fluoride (HF) or boron trifluoride ($BF_3$) molecules, transferring the negative charge to the rest of the molecule. Such a fragmentation pattern is used to detect and quantitate analytes of interest after derivatization with organo-trifluoroborates.

20 Claims, 17 Drawing Sheets

Fragmentation pathways of organo-*bis*-trifluoroborates.

$^2R$, $^3R$ = Organic moiety or molecule
$X^\oplus$ = any positively charged counter ion

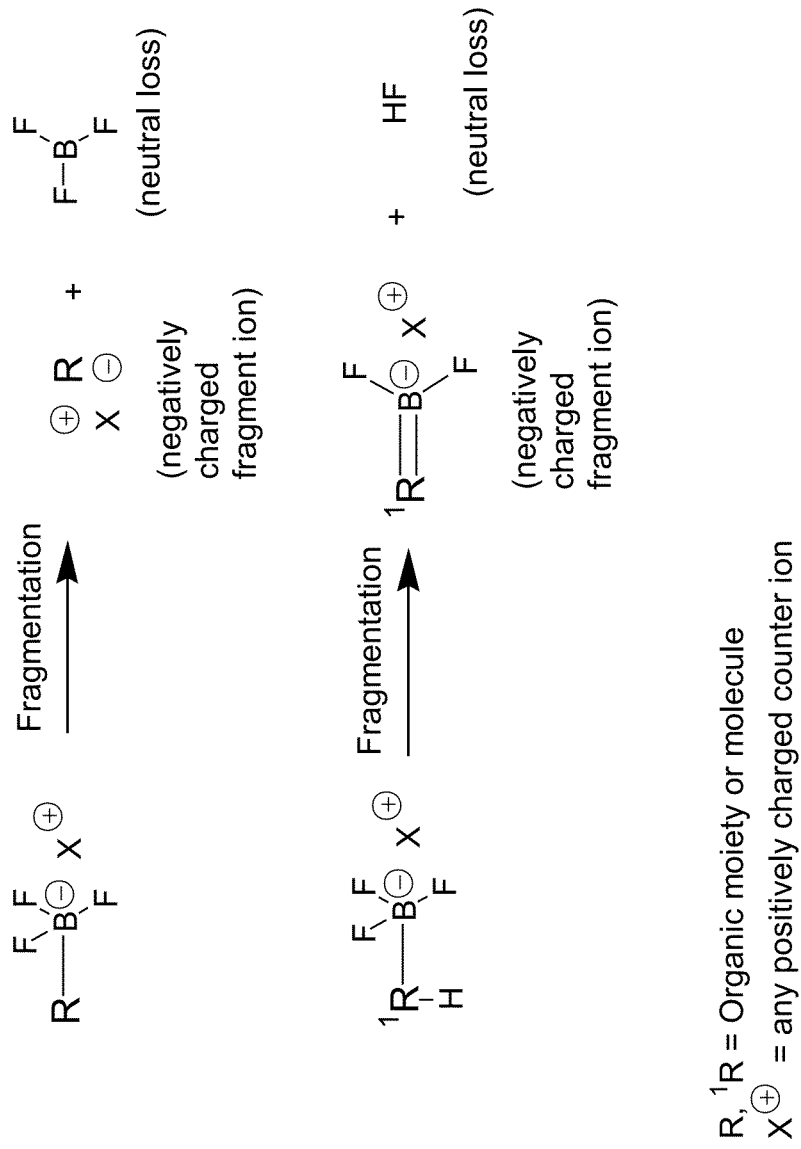
FIG. 1. Fragmentation pathways of organo-trifluoroborates.

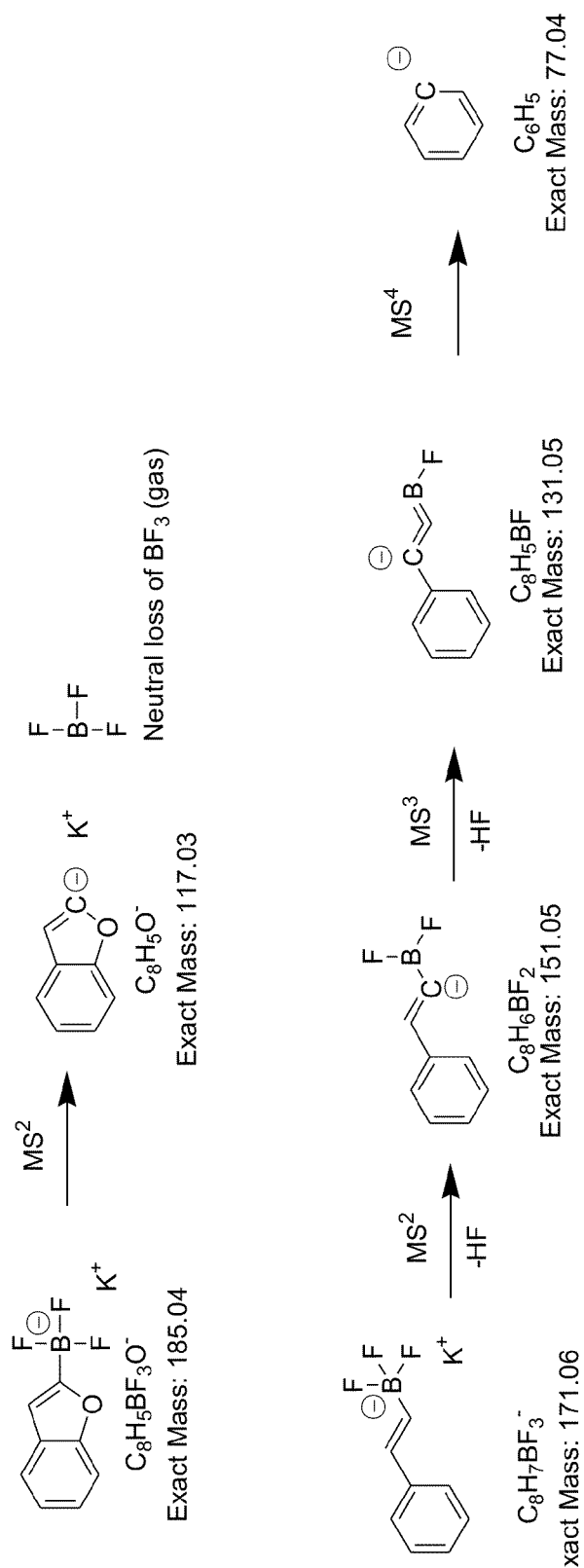
FIG. 2. Predictable fragmentation pathways of two organo-trifluoroborates (Note: the mass spectra of these pathways are shown in FIG. 3 and FIG. 4).

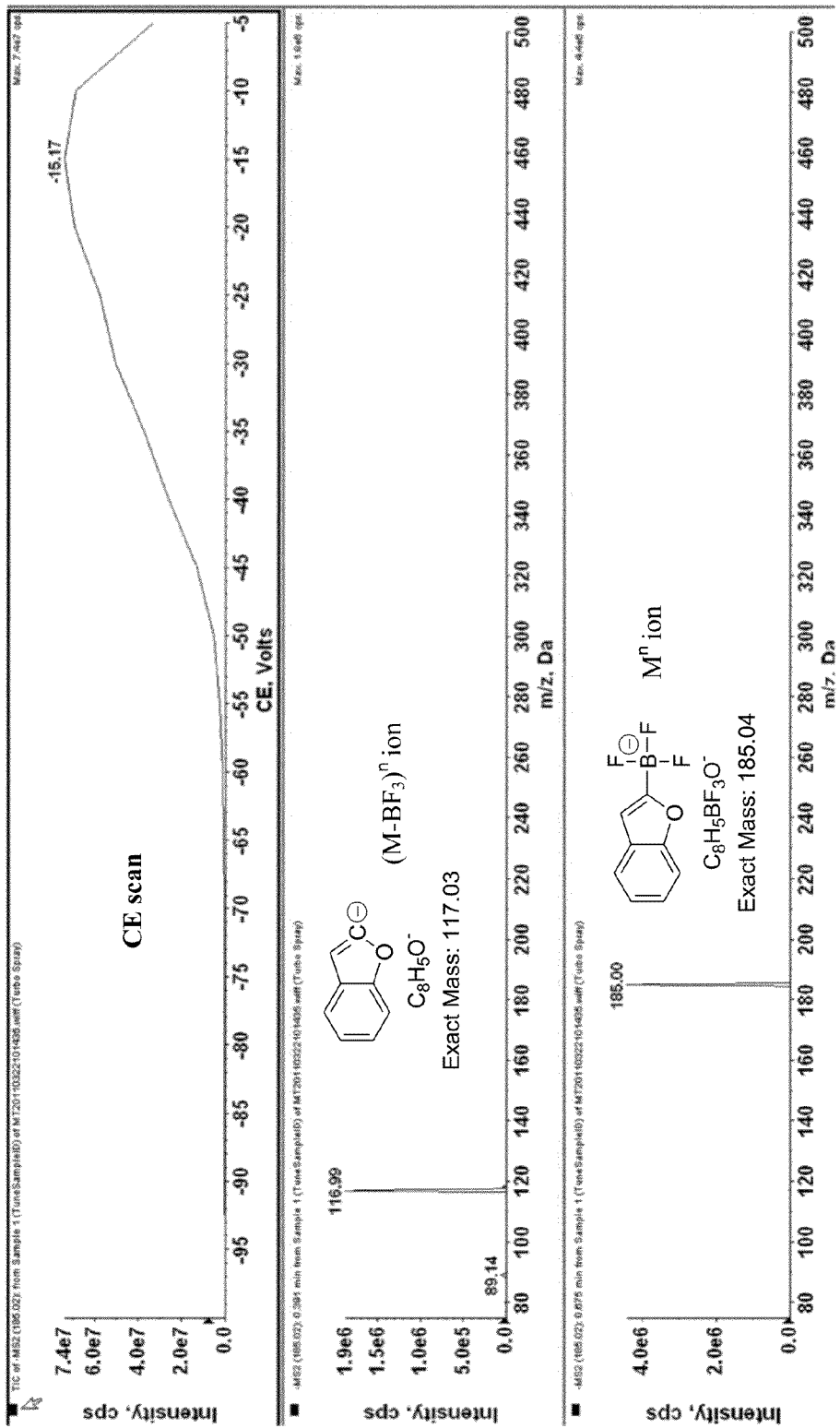
FIG. 3. Collisional energy (CE) scan of potassium benzofuran-2-trifluoroborate. Fragmentation at CE = -45 ev shows the predictable fragment with $BF_3$ as a neutral loss.

FIG. 4. Collisional energy (CE) scan of potassium trans-styryltrifluoroborate. Fragmentation at CE = −45, −30, and −15 ev shows the predictable fragments with HF and CH=CHBF₃ as neutral losses.
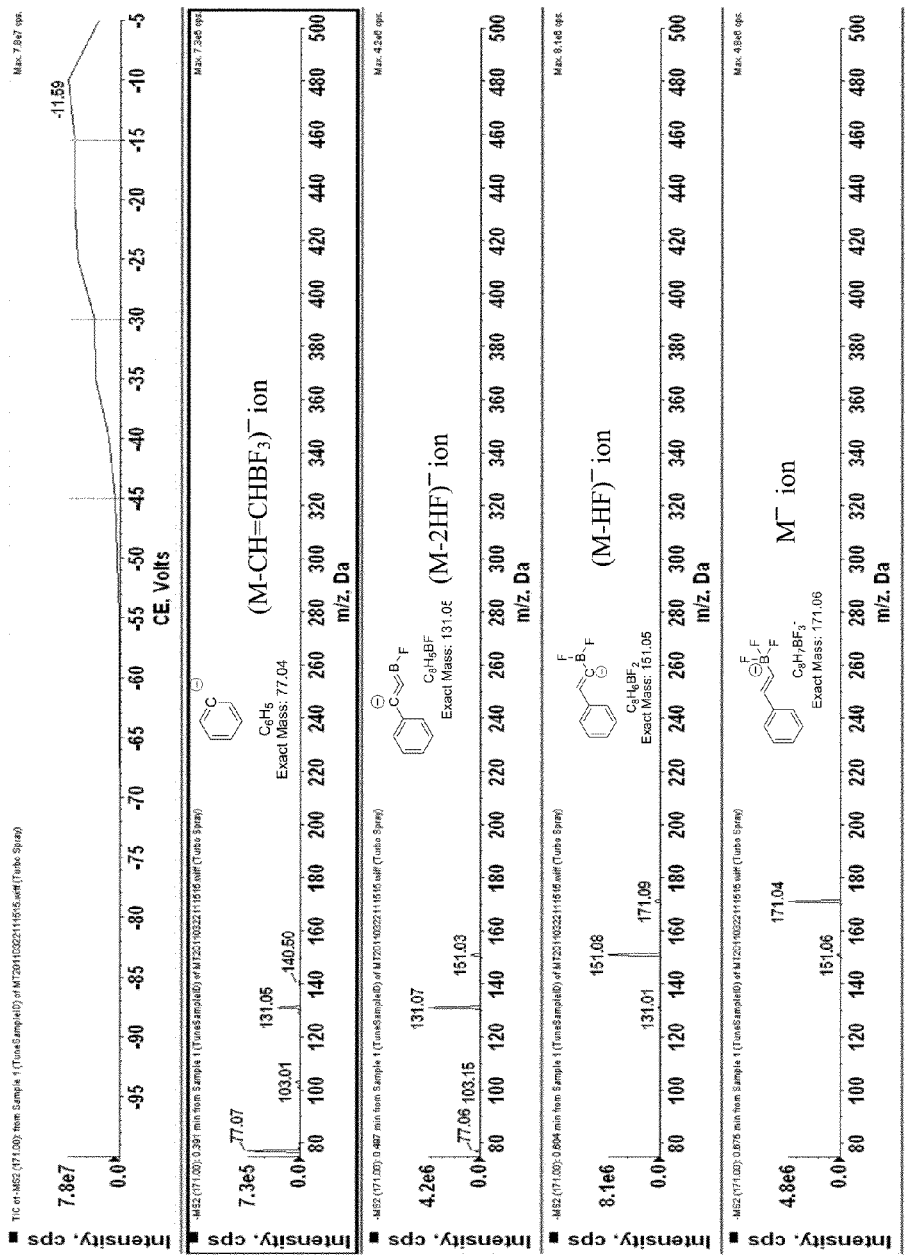

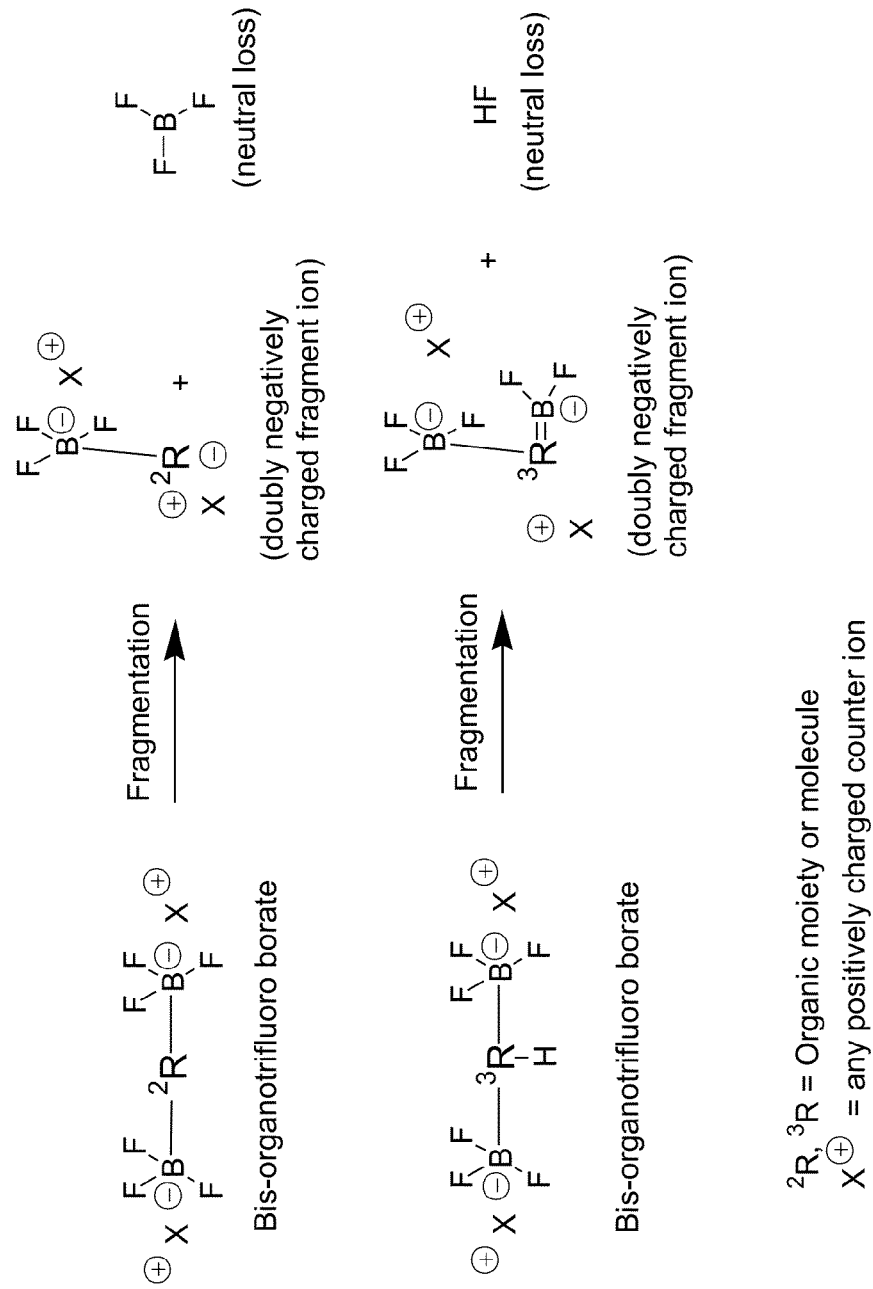
FIG. 5. Fragmentation pathways of organo-*bis*-trifluoroborates.

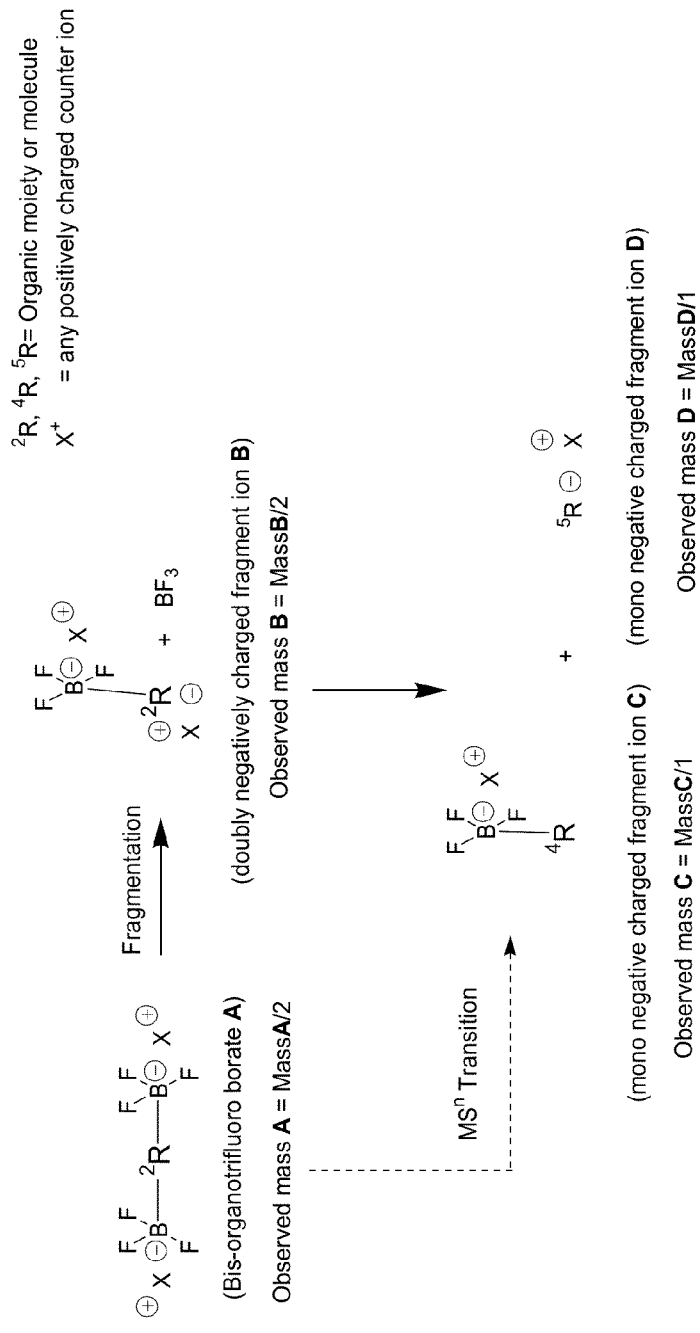
FIG. 6. Low to high mass parent-daughter ion monitoring in negative ion mode.
If fragmentation pathway is such that mass of frament C > 1/2 mass of A then transtion from A→C will be lower to higher mass transtion (observed)
If fragmentation pathway is such that mass of frament D > 1/2 mass of A then transtion from A→D will be lower to higher mass transtion (observed)

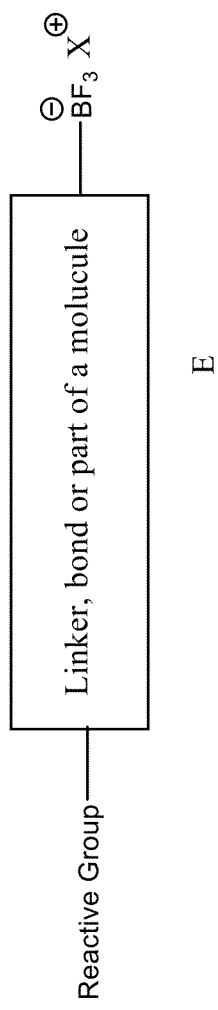

FIG. 7. Trifluoroborate-containing mass tags E.

Reactive group = alcohol, diene, dienophile, carboxylic acid, amine, thiols, alkyl halides, ketone, aldehydes, aminooxy, hydrazine and its derivatives, activated esters, acid halides, isocyanate, and thio-isocyanate, azo, alkyne, 1,3-dipolariphile, sulfonyl chloride group, glyoxals, an epoxide or oxiranes, a carbonate group, aryl halide group such as fluorobenzene derivatives, a imidoester or imidate funcational group, an anhydride group, a fluorophenyl ester, a hydroxymethyl phosphine derivative, maleimide group, aziridine group, acryloyl derivative group, arylating agent such as derviatives of benzene which possess either halogen or sulfonate groups on the ring, thiol-disulfide exchange reagent such as pyridyl dithiol and thiolnitrobenzoic acid group, vinylsulfone group

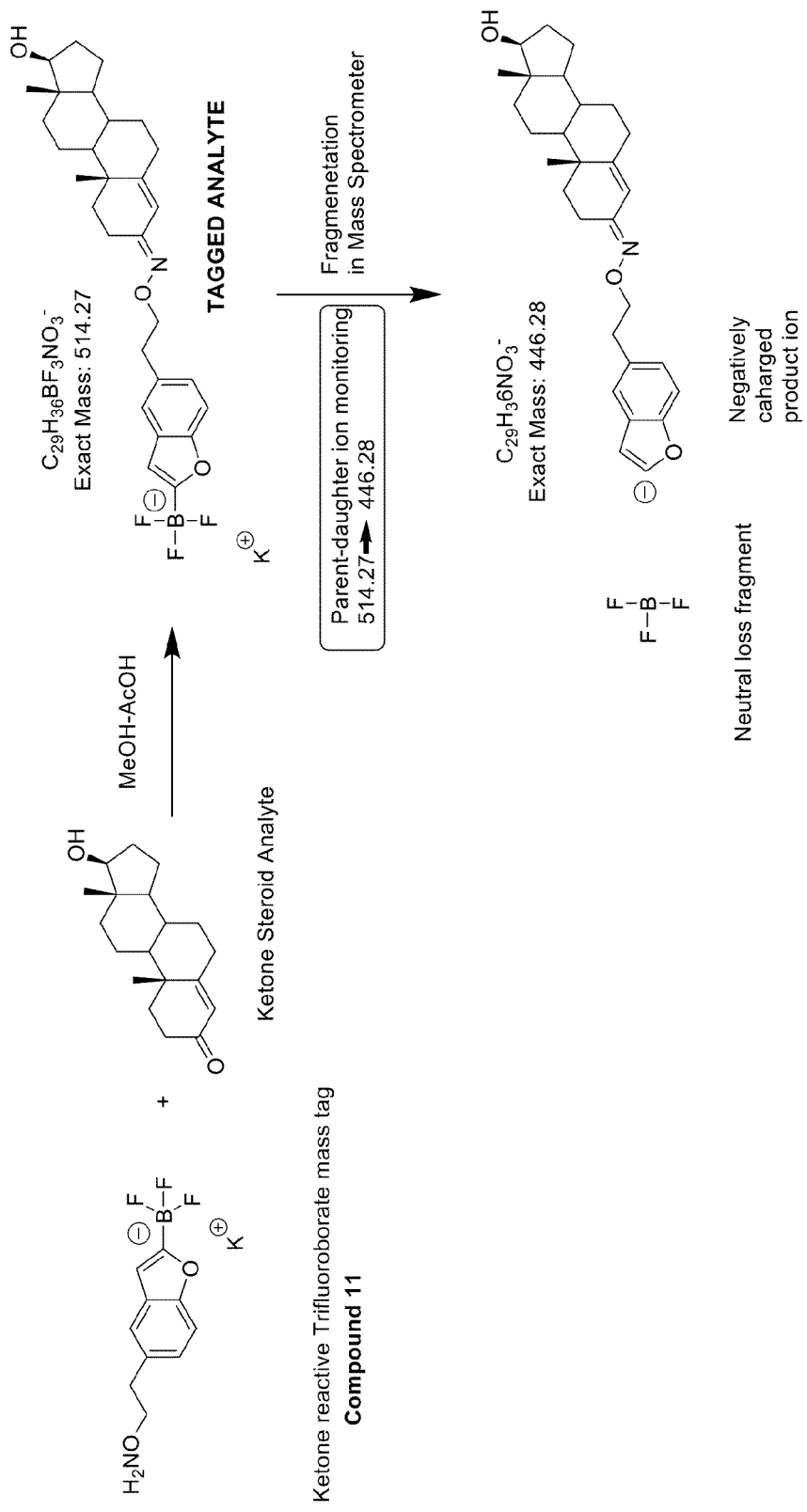
FIG. 8. A schematic example of a reaction of a Ketone-reactive trifluoroborate mass tag with an ketone analyte and fragmentation of the tagged analyte in a mass spectrometer.

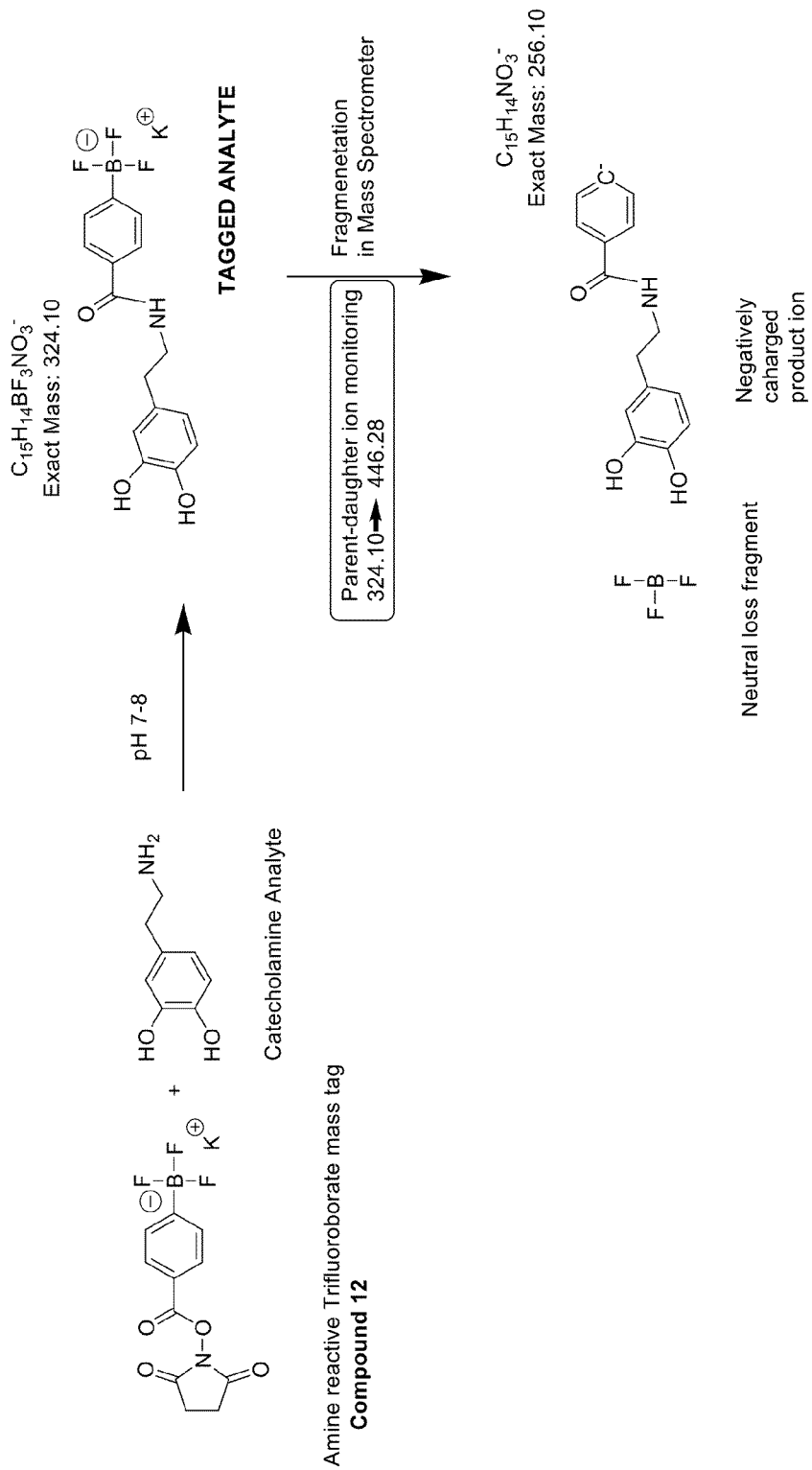
FIG. 9. A schematic example of a reaction of an amine-reactive trifluoroborate mass tag with amine analyte and fragmentation of the tagged analyte in a mass spectrometer.

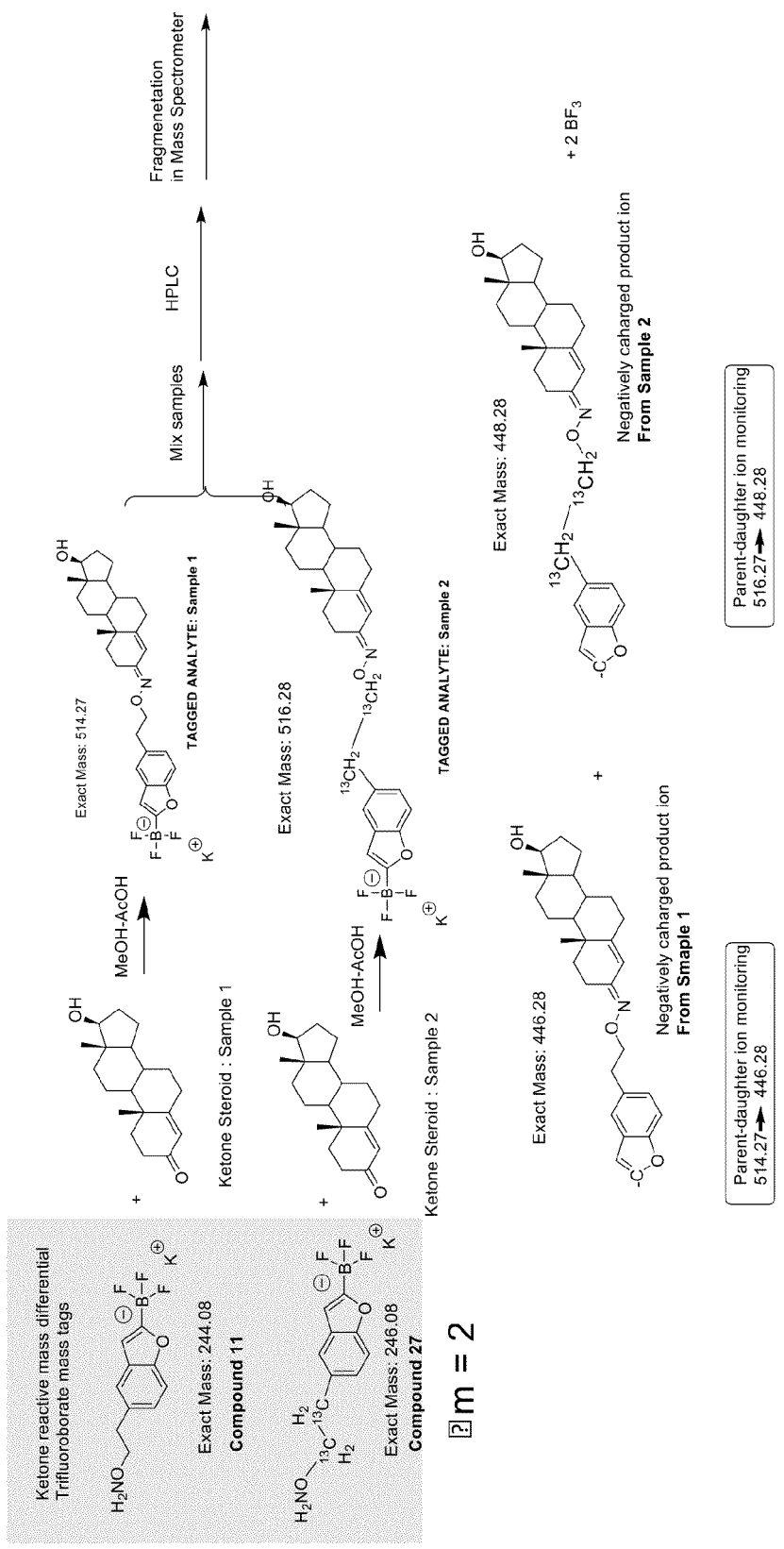

FIG. 10. A schematic example of ketone-reactive mass-differential trifluoroborate mass tags. Such a mass tag is reacted with a ketone analyte from two different samples. After derivatization with the mass tags, samples are mixed and analyzed by LC-MS/MS. Because of the difference in the mass of parent-daughter ions, multiple (in this case two) samples can be analyzed in one LC-MS/MS run, increasing the throughput of analysis.

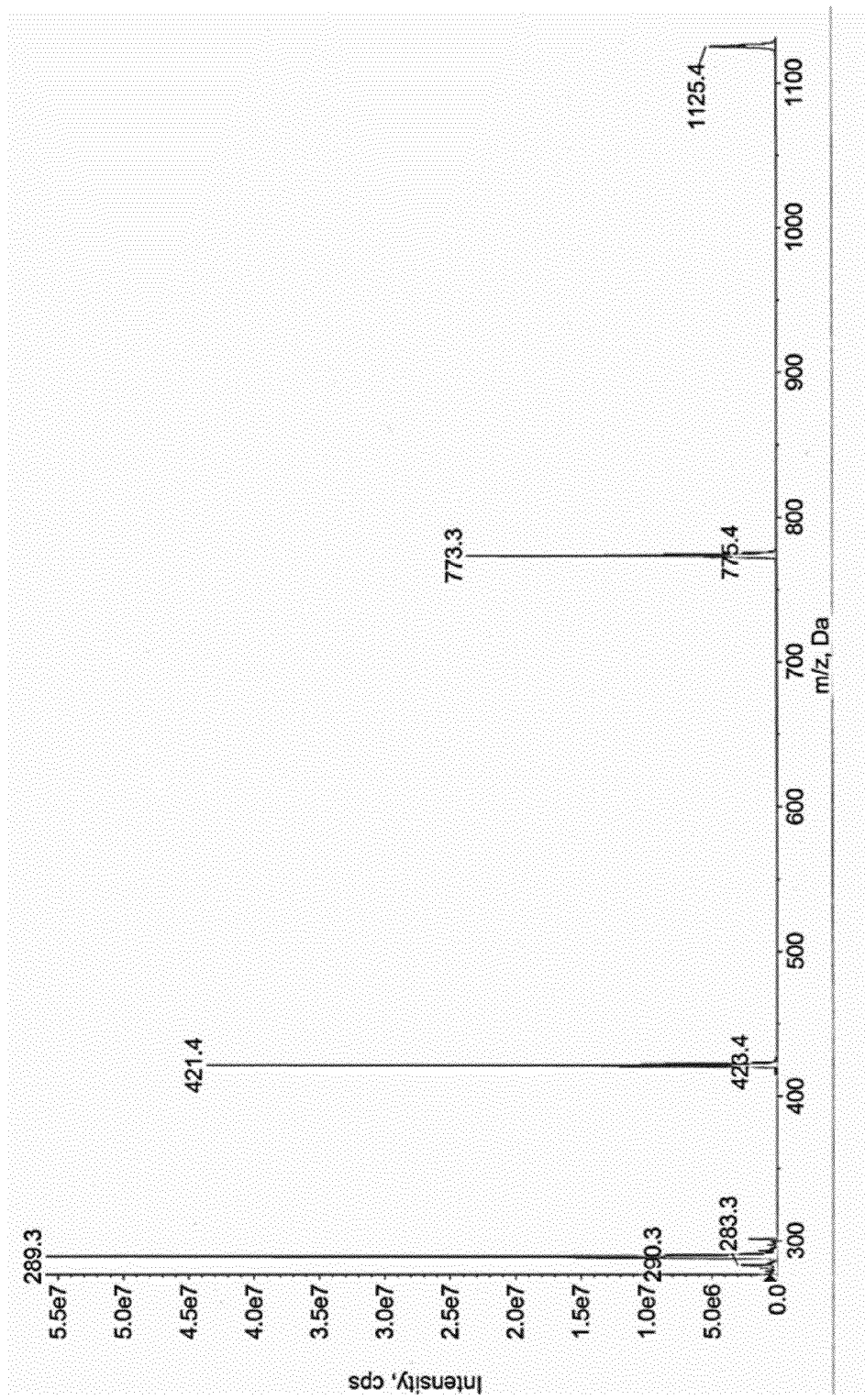
FIG. 11. Q1-MS scan (low resolution) of a mixture of compound 23, 24, 25 and 26 infused directly as methanol-water solution. Calculated most abundant isotopic mass of the m-dPEG-trifluoroborates are Compound 23 ($C_{10}H_{21}O_5BF_3^-$): 289.1; Compound 24 ($C_{16}H_{33}O_8BF_3^-$): 421.2; Compound 25 ($C_{32}H_{65}O_{16}BF_3^-$): 773.4; Compound 26 ($C_{48}H_{97}O_{24}BF_3^-$): 1125.6

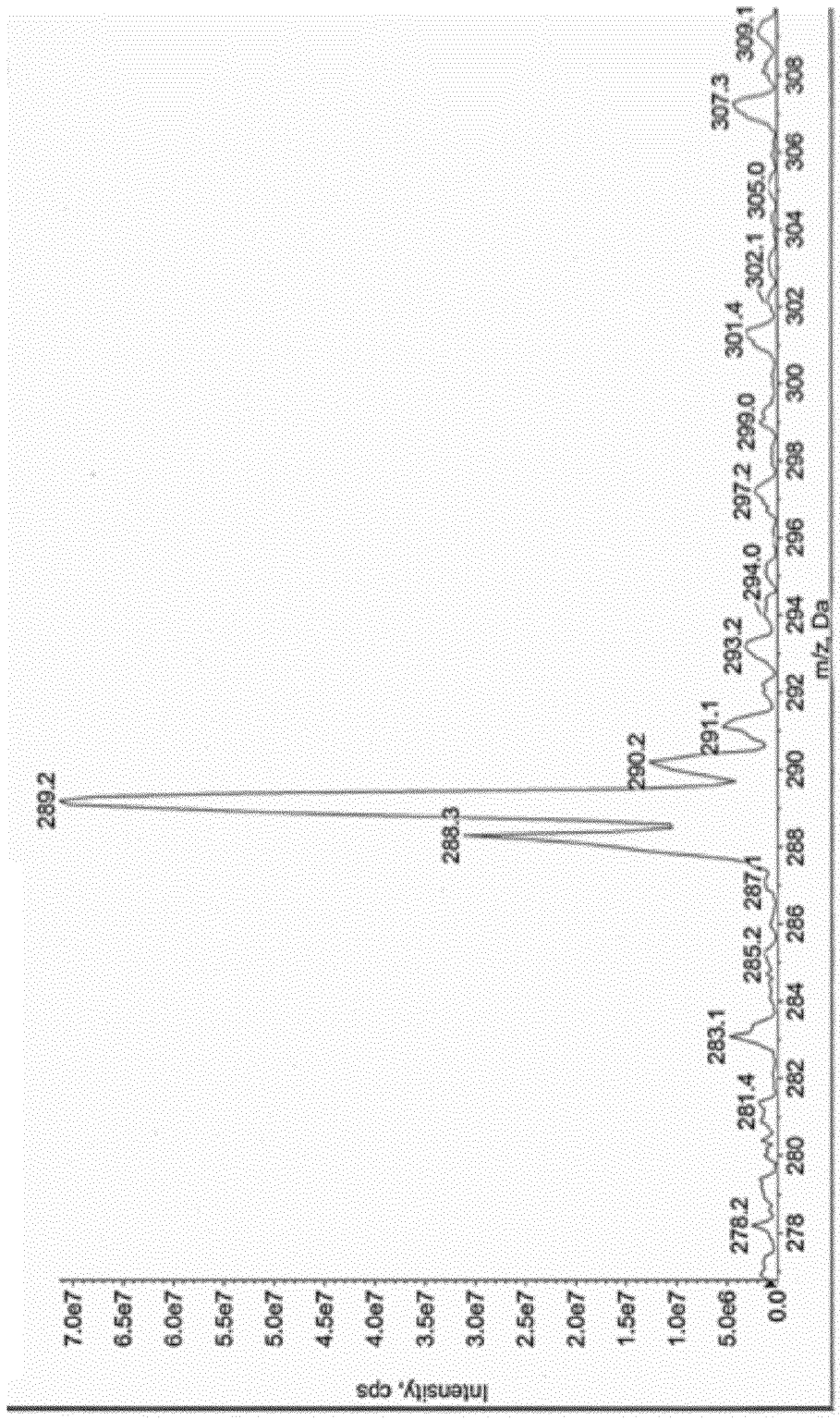
FIG. 12. Q1-MS scan (low resolution) of a mixture of compound 23, 24, 25 and 26 infused directly as methanol-water solution. Contributions of $^{10}B$ isotope are seen as a peak at 1 amu less left to the major isotopic peak containing $^{11}B$ isotope.
A.

B.

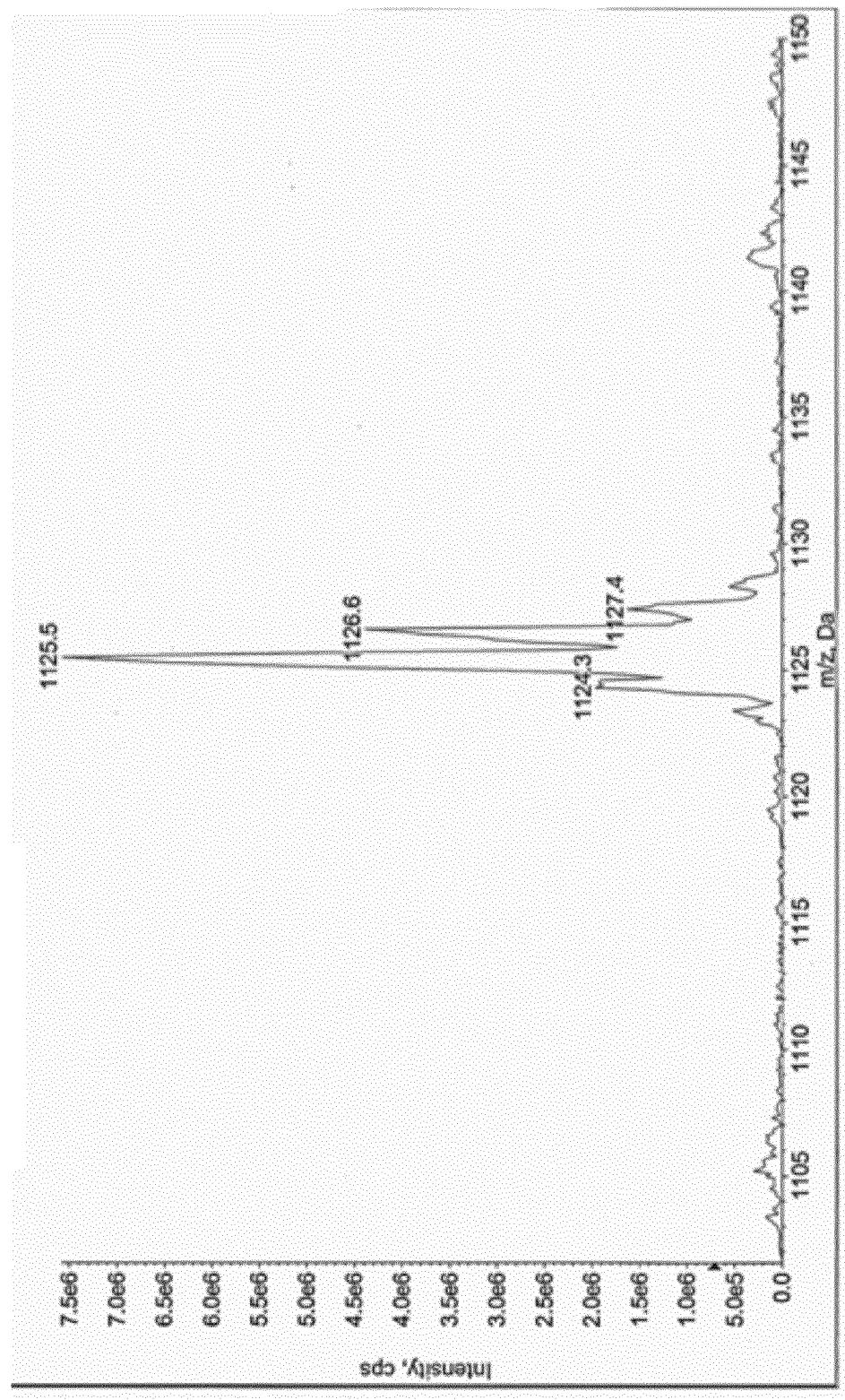
FIG. 12 (CONT'D) D.

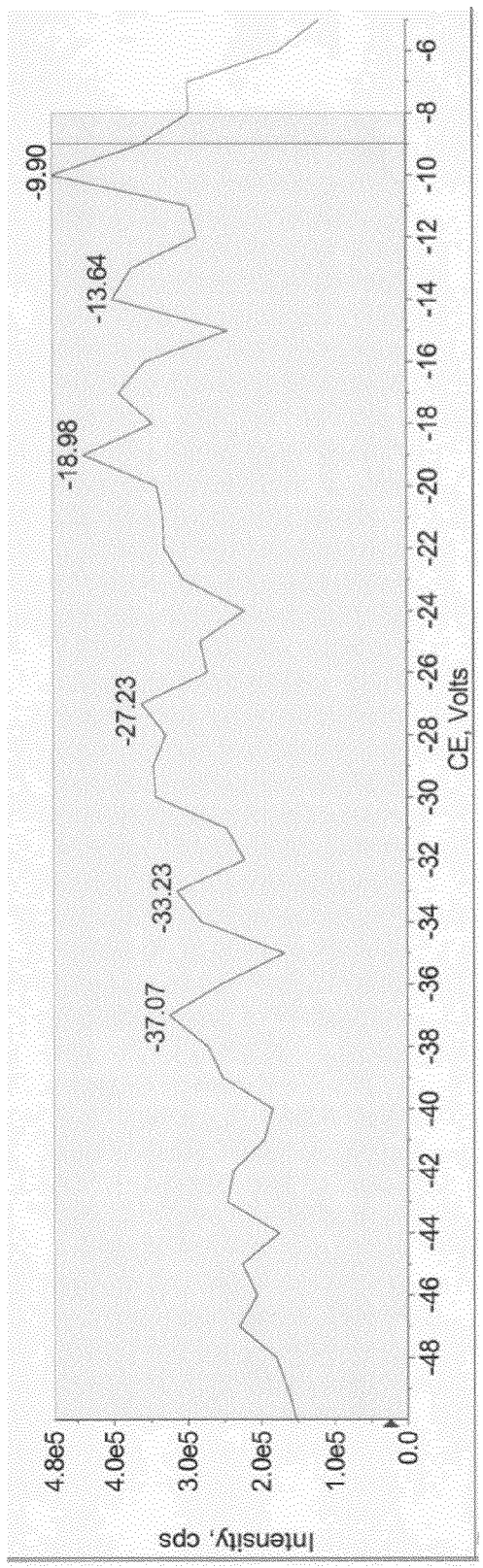
FIG. 13 is MS/MS fragmentation of compound 2 forming predictable fragments.

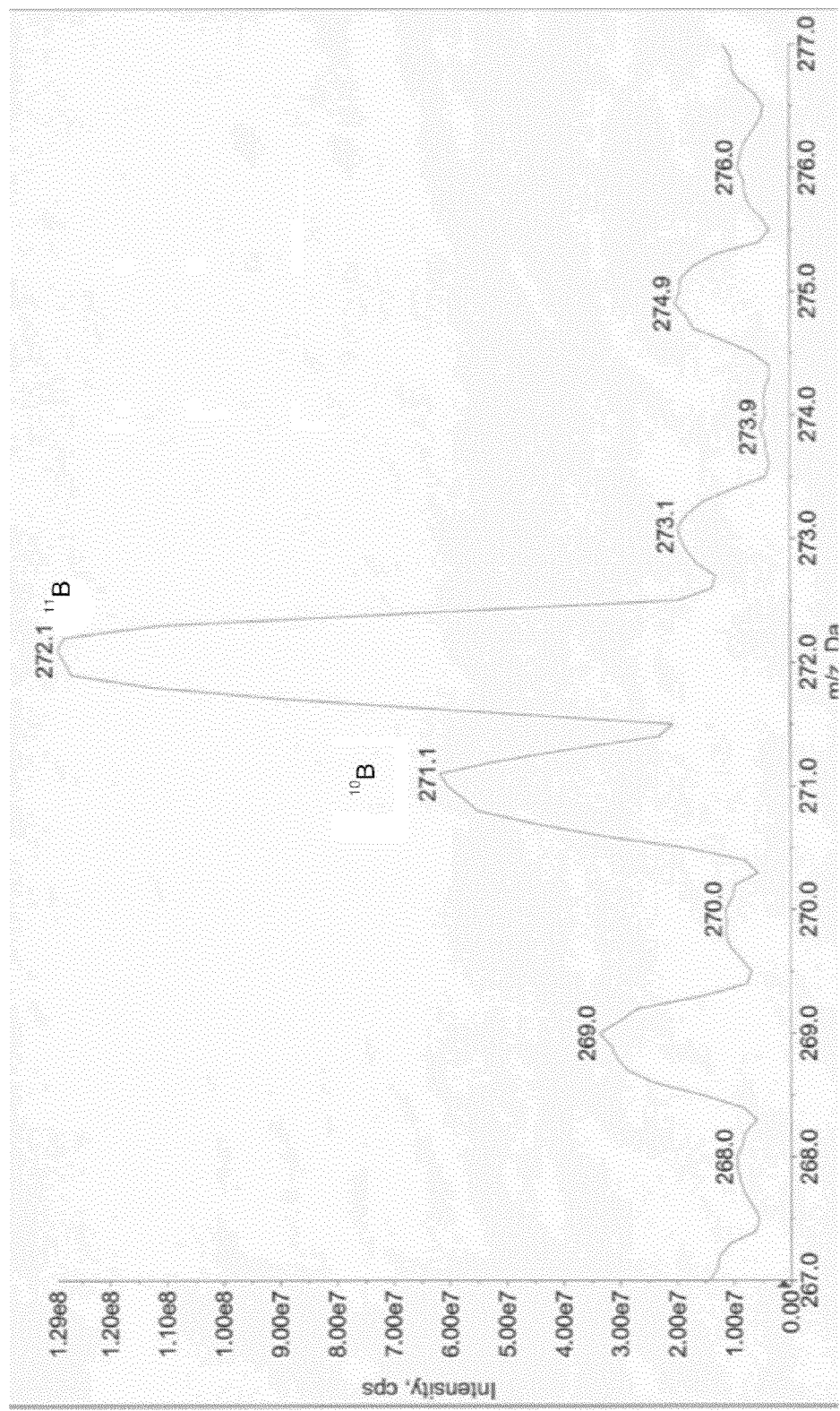
FIG. 14 shows isotopic distribution of compound 2 showing presence of $^{10}$B and $^{11}$B.

TRIFLUOROBORATE MASS SPECTROMETRIC TAGS

PRIORITY CLAIMS AND RELATED APPLICATIONS

This application is the U.S. national phase of and claims priority to PCT/US2014/031795, filed Mar. 26, 2014, which claims the benefit of priority from U.S. Provisional Application Ser. No. 61/805,644, filed on Mar. 27, 2013, the entire content of each of which is incorporated herein by reference in its entirety.

FIELD OF THE INVENTION

The invention provides compounds and compositions of organoborates (e.g., organo-trifluoroborates) and related methods and use thereof in mass spectroscopy. More particularly, the invention provides organo-trifluoroborates and their applications in mass spectroscopy as mass tag reagents or kits for qualitative and quantitative analysis in parent ion or parent-daughter ion monitoring mode.

BACKGROUND OF THE INVENTION

The presence of positively charged groups, such as amine under acidic buffer conditions, quaternary amine functionality, or other electropositive groups in various analytes, is common. Mass spectrometry has been widely used to analyze such molecules in various modes, including $MS^2$ or $MS^3$ modes. Such applications are now standard practice for the analysis of clinically relevant analytes, such as peptides, proteins, and small molecules. Various mass tag reagents have been strategically designed that are or can be positively charged under acidic buffer conditions to conjugate or react with different classes of analytes and impart a positive charge to the overall molecule. Such tags can then be used to enhance signal intensity in positive ion mode analysis and for relative or absolute quantitation.

Unlike mass spectrometric analysis in positive mode, analysis in negative mode is not common. This disparity is partially due to a lack of electronegative groups or functionalities at our disposal. For example, carboxylic (—COOH), phosphoric (—OPO(OH)$_2$), or sulfonic (—SO$_3$H) functional groups can be ionized under basic conditions to produce negatively charged species, but the degree of ionization is highly dependent on the pH of the media. Mass spectrometric analysis under basic conditions has drawbacks, including limited variety and stability of volatile buffers and the instability of reversed phase HPLC columns under basic conditions.

There is an ongoing need for mass tag reagents that are suitable for use in negative ion mode mass spectrometry.

SUMMARY OF THE INVENTION

The present invention relates to the application and use of organo-trifluoroborates in the negative ion mode mass spectrometry field, as well as the preparation of novel mass-tags designed specifically for different analytes. The invention is based, in part, on the discovery that organo-trifluoroborates, when subject to fragmentation, such as with collision-induced dissociation (CID), preferentially undergo neutral losses of hydrogen fluoride (HF) or boron trifluoride (BF$_3$), transferring the negative charge to the rest of the fragment molecule.

The invention is also based, in part, on our discovery that the negatively charged fragment formed upon collision-induced dissociation of organo-trifluoroborate and neutral loss of hydrogen fluoride (HF) or boron trifluoride (BF$_3$) can be further fragmented in $MS^n$ (n=integer) mode to generate smaller, predictable, negatively charged molecular fragments. Such a fragmentation pathway is directed by the kinetic or thermodynamic stability of the fragmentation product.

In one aspect, the invention generally relates to a method for mass spectrometric analysis, comprising fragmenting organo-trifluoroborate mass tags or an analyte tagged with one or more organo-trifluoroborate mass tags comprising one or more trifluoroborate groups in negative ion mode to produce one or more negatively charged fragment ions and one or more molecules with no charge (neutral losses). In certain embodiments, the method further includes detecting one or more negatively charged fragment ions.

In some embodiments, the mass spectrometric method can be used for qualitative or quantitative monitoring and analysis of organo-trifluoroborate-tagged analytes or a panel of analytes.

In another aspect, the invention generally relates to a mass spectrometric process by which an organo-multi-trifluoroborate or organo-multi-trifluoroborate containing mass tags undergoes fragmentation in negative ion mode to produce fragment ions that are mono-negative or multi-negative, structure-specific daughter ion(s).

In some embodiments, such a mass spectrometric process can be used to generate methods for qualitative or quantitative monitoring and analysis of organo-multi-trifluoroborate tagged analytes or a panel of analytes.

In some embodiments, during the fragmentation studies, the fragmentation energy is zero.

In yet another aspect, the invention generally relates to the usage or application of organo-trifluoroborate compounds or mass tags having general formula E in negative ion mass-spectrometric applications.

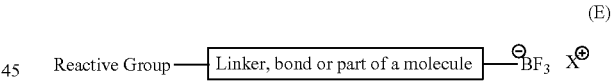

(E)

wherein the reactive group is selected from the group consisting of an alcohol, alkoxy, aryloxy, diene, dienophile, carboxylic acid, amine, thiol, alkyl halide, ketone, aldehyde, aminooxy, hydrazine and its derivatives, activated ester, acid halide, isocyanate or thio-isocyanate, azo, alkyne, 1,3-dipolariphile, sulfonyl chloride, glyoxal, epoxide or oxirane, carbonate, aryl halide such as fluorobenzene derivatives, imidoester or imidate, anhydride, fluorophenyl ester, hydroxymethyl phosphine derivative, maleimide, aziridine, acryloyl derivative, arylating agent such as derivatives of benzene that possess either halogen or sulfonate groups on the ring, thiol-disulfide exchange reagent such as pyridyldithiol and thiolnitrobenzoic acid, or vinylsulfone group; L is a bond, linker, spacer, or part of a molecule; and $X^\oplus$ is a positively charged counter ion.

In some embodiments, the invention generally relates to usage or application of organo-trifluoroborate compounds or mass tags having the general formula (EI) in negative ion mass-spectrometric analysis.

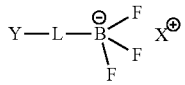
(EI)

wherein

Y is a reactive group selected from the group consisting of an alcohol, alkoxy, aryloxy, diene, dienophile, carboxylic acid, amine, thiol, alkyl halide, ketone, aldehyde, aminooxy, hydrazine and its derivatives, activated ester, acid halide, isocyanate or thio-isocyanate, azo, alkyne, 1,3-dipolariphile, sulfonyl chloride, glyoxal, epoxide or oxirane, carbonate, aryl halide such as fluorobenzene derivatives, imidoester or imidate, anhydride, fluorophenyl ester, hydroxymethyl phosphine derivative, maleimide, aziridine, acryloyl derivative, arylating agent such as derivatives of benzene that possess either halogen or sulfonate groups on the ring, thiol-disulfide exchange reagent such as pyridyldithiol and thiolnitrobenzoic acid, or vinylsulfone group; and L is a bond or linker; and $X^\oplus$ is a positively charged counter ion.

In some embodiments, $X^\oplus$ is a positively charged counter ion selected from the group consisting of $K^+$, $Cs^+$, $Rb^+$, quaternary ammonium, pyridinium, pyrazolium, thiazolium, morpholium, triazolium, imidazolium, bezoxazolium, thiadiazolium, oxadiazolium, and guanidinium ions. In a preferred embodiment, $X^\oplus$ is $K^+$.

In some embodiments, L is a linker or a combination of two or four linkers that independently selected from the group consisting of ethylene glycol, propylene glycol, methylene, a peptide, a peptidomimetic oligomer, substituted or un-substituted heteroalicyclyl $C_1$-$C_{12}$ alkyl, —(CH$_2$CH$_2$O)$_{1-36}$—, —(CH$_2$CH$_2$O)$_{1-36}$—CH$_2$—, substituted or un-substituted alicyclyl, heteroalicyclyl, substituted or un-substituted aryl, —C(=G$^2$)-G$^1$, -G$^1$-C(=G$^2$)-, -G$^3$-, -G$^1$-C(=G$^2$)-G$^1$, —S—S—, —S—(CH$_2$)$_2$—S(O)$_2$—, —S(O)$_2$—(CH$_2$)$_2$—S—, —S(O)$_2$—N(R$^3$)—, —N(R$^3$)—S(O)$_2$—, —C(O)—NH—NH—CH$_2$—, —C(O)—NH—N=CH—, —CH=N—NH—C(O)—, —CH$_2$—NH—NH—C(O)—, —N(R$^3$)—S(O)$_2$—N(R$^3$)—, —C(O)—NH—CH(CH$_2$SH)—, —N=CH—, —NH—CH$_2$—, —NH—C(O)—CH$_2$—C(O)—NH—, —CH=N-G$^4$-, —CH$_2$—NH-G$^4$-, G$^4$-NH—CH$_2$—, -G$^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—P(=O)(S$^-$)—O—, —O—P(=S)(S$^-$)—O—,

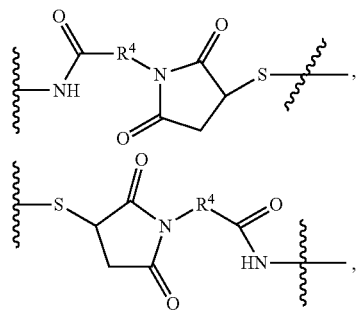

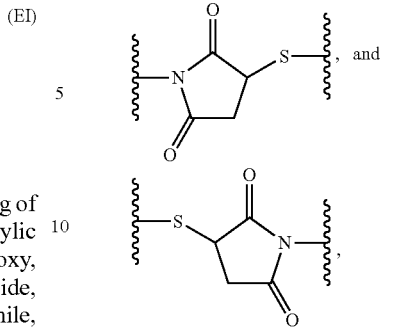

wherein each $G^1$ is independently selected from NR$^3$, O, and S; each $G^2$ is independently O or S; each $G^3$ is independently selected from S, O, NR$^3$, and SO$_2$; each $G^4$ is independently O or NR$^3$; each R$^3$ is independently selected from hydrogen, $C_1$-$C_8$ alkyl, —(OCH$_2$CH$_2$)$_{1-3}$, optionally substituted alicyclyl, and optionally substituted heteroalicyclyl; each R$^4$ is independently $C_1$-$C_8$ alkyl, —(OCH$_2$CH$_2$)$_{1-3}$, optionally substituted alicyclyl, and optionally substituted heteroalicyclyl.

In yet another aspect, the invention generally relates to usage of an organo-bis-trifluoroborate compound having general formula A in negative ion mass-spectrometric applications:

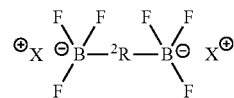
(A)

wherein $^2R$ is an organic moiety or molecule; and $X^\oplus$ is a positively charged counter ion.

In yet another aspect, the invention generally relates to usage or application of organo-bis-trifluoroborate compounds or mass tags having general formula AI in negative ion mass-spectrometric analysis.

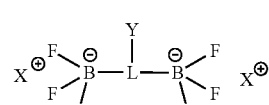
(AI)

wherein

Y is a reactive group selected from the group consisting of an alcohol, alkoxy, aryloxy, diene, dienophile, carboxylic acid, amine, thiol, alkyl halide, ketone, aldehyde, aminooxy, hydrazine and its derivatives, activated ester, acid halide, isocyanate or thio-isocyanate, azo, alkyne, 1,3-dipolariphile, sulfonyl chloride, glyoxal, epoxide or oxirane, carbonate, aryl halide such as fluorobenzene derivatives, imidoester or imidate, anhydride, fluorophenyl ester, hydroxymethyl phosphine derivative, maleimide, aziridine, acryloyl derivative, arylating agent such as derivatives of benzene that possess either halogen or sulfonate groups on the ring, thiol-disulfide exchange reagent such as pyridyldithiol and thiolnitrobenzoic acid, or vinylsulfone group; and L is a bond or linker; and $X^\oplus$ is a positively charged counter ion.

In some embodiments, $X^\oplus$ is a positively charged counter ion selected from the group consisting of $K^+$, $Cs^+$, $Rb^+$, quaternary ammonium, pyridinium, pyrazolium, thiazolium, morpholium, triazolium, imidazolium, bezoxazolium, thiadiazolium, oxadiazolium and guanidinium ions. In a preferred embodiment, $X^\oplus$ is $K^+$.

In some embodiments, L is a linker or a combination of two or four linkers that independently selected from the group consisting of ethylene glycol, propylene glycol, methylene, a peptide, a peptidomimetic oligomer, substituted or un-substituted heteroalicyclyl $C_1$-$C_{12}$ alkyl, —$(CH_2CH_2O)_{1-36}$—, —$(CH_2CH_2O)_{1-36}$—$CH_2$—, substituted or un-substituted alicyclyl, heteroalicyclyl, substituted or un-substituted aryl, —C(=$G^2$)-$G^1$-, -$G^1$-C(=$G^2$)-, -$G^3$-, -$G^1$-C(=$G^2$)-$G^1$-, —S—S—, —S—$(CH_2)_2$—S$(O)_2$—, —S$(O)_2$—$(CH_2)_2$—S—, —S$(O)_2$—N($R^3$)—, —N($R^3$)—S$(O)_2$—, —C(O)—NH—NH—$CH_2$—, —C(O)—NH—N=CH—, —CH=N—NH—C(O)—, —$CH_2$—NH—NH—C(O)—, —N($R^3$)—S$(O)_2$—N($R^3$)—, —C(O)—NH—CH($CH_2SH$)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=$NH_2^+$)—NH—, —NH—C(=$NH_2^+$)—, —O—P(=O)($O^-$)—NH—, —NH—P(=O)($O^-$)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, —O—P(=S)($S^-$)—O—,

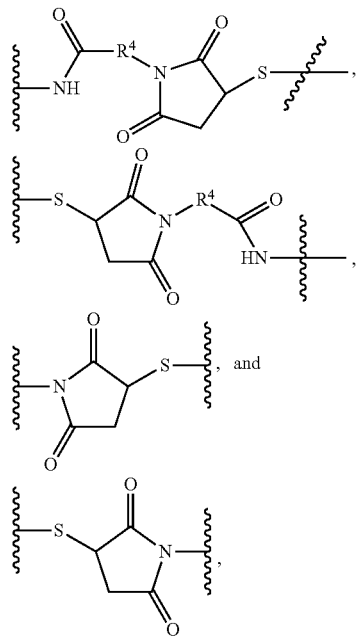

wherein each $G^1$ is independently selected from $NR^3$, O, and S; each $G^2$ is independently O or S; each $G^3$ is independently selected from S, O, $NR^3$, and $SO_2$; each $G^4$ is independently O or $NR^3$; each $R^3$ is independently selected from hydrogen, $C_1$-$C_8$ alkyl, —$(OCH_2CH_2)_{1-3}$, optionally substituted alicyclyl, and optionally substituted heteroalicyclyl; each $R^4$ is independently $C_1$-$C_8$ alkyl, —$(OCH_2CH_2)_{1-3}$, optionally substituted alicyclyl, and optionally substituted heteroalicyclyl.

In some embodiments, organo-borate compounds or organo-borate mass tags of general formula E, E1, A, or AI are labeled at specific sites within the molecule using heavy stable isotopes, including but not limited to $^{10}$B and $^{11}$B, $^{12}$C and $^{13}$C, $^{14}$N and $^{15}$N, $^{16}$O and $^{18}$O, $^{1}$H and $^{2}$H isotopes, or a combination of these isotopes, to generate a set of isobaric or mass differential tags or reagents. Such a set of reagents can be used in a multiplexed format to speed up analysis. Such a set of reagents can be used for absolute and relative quantitation of analytes in negative ion mode. Such a set of reagents can be used for absolute and relative quantitation of analytes in a multiplexed format in negative ion mode.

In some embodiments, organo-borate compounds or organo-borate mass tags of general formula E, E1, A, or AI wherein a combination of heavy stable isotopes, including but not limited to $^{10}$B and $^{11}$B, $^{12}$C and $^{13}$C, $^{14}$N and $^{15}$N, $^{16}$O and $^{18}$O, or $^{1}$H and $^{2}$H isotopes, are used in such a way that the total additional mass due to heavy isotopes is distributed between the reactive group, linker, and trifluoroborate moiety to produce a set of isobaric mass tags. In such a case, a set of isobaric multiplexing reagents can be generated for parallel or simultaneous analysis.

In some embodiments, organo-borate compounds or organo-borate mass tags of general formula E, E1, A, or AI wherein a combination of heavy stable isotopes, including but not limited to $^{10}$B and $^{11}$B, $^{12}$C and $^{13}$C, $^{14}$N and $^{15}$N, $^{16}$O and $^{18}$O, or $^{1}$H and $^{2}$H isotopes, are used in such a way that the additional mass due to heavy isotopes is distributed between the reactive group, linker, and trifluoroborate moiety to produce a set of mass differential tags. In such a case a set of mass differential multiplexing reagents can be generated for parallel or simultaneous analysis.

In some embodiments, the organo-borate compounds or organo-borate mass tags of general formula E, E1, A, or AI may be connected to a reactive group via a linker, spacer, or bond. The reactive group is designed to react specifically with the analyte of interest, depending on the functional group present in the analyte.

In another aspect, the invention generally relates to an organo-trifluoroborate compound having structural formula EII:

(EII)

wherein $Y^1$ is a reactive group selected from the group consisting of alcohol, alkoxy, a diene, dienophile, aminooxy, activated ester, N-hydroxysuccinimide ester, alkyl halide, aryl halide, maleimide, thiol-disulfide exchange reagent such as pyridyldithiol and thiolnitrobenzoic acid, or vinylsulfone group;

$L^1$ is a linker or a combination of 2 to 4 linkers that individually selected from the group consisting of $C_1$-$C_{20}$ alkyl, —$(CH_2CH_2O)_{1-36}$—, —$(CH_2CH_2O)_{1-36}$—$CH_2$—, a peptide, a peptidomimetic oligomer, alicyclyl, optionally substituted alicyclyl, heteroalicyclyl, optionally substituted heteroalicyclyl, optionally substituted aryl; and $X^\oplus$ is a positively charged counter ion.

In some embodiments, the organo-trifluoroborate compound of general formula EII is labeled with one or more stable heavy isotopes selected from $^{10}$B and $^{11}$B, $^{12}$C and $^{13}$C, $^{14}$N and $^{15}$N, $^{16}$O and $^{18}$O, and $^{1}$H and $^{2}$H isotopes at select atomic sites such that the total additional mass due to heavy isotope labeling is distributed between the reactive group, the linker, and trifluoroborate group to produce a set of isobaric and mass differential tags.

In some preferred embodiments, $Y^1$ of the organo-trifluoroborate compound of the general formula EII is an aldehyde and ketone reactive aminooxy (—ONH$_2$) group. In another preferred embodiment, $Y^1$ is an amine reactive N-hydroxysuccinimide ester group. In another preferred embodiment, $Y^1$ is a diene reactive group having the following structural formula:

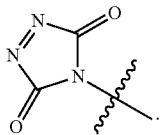

In some embodiments, linker (L) of the organo-trifluoroborate compound of the general formula E11 has a benzofuran core structure with the following structural formula:

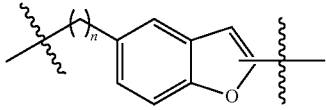

wherein n is 0 or an integer selected from 1 to about 12.

In some embodiments, Y1 is an aldehyde and ketone reactive aminooxy group. In another embodiment, $Y^1$ is a diene reactive group having the following structural formula:

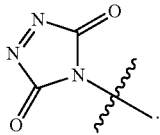

In some embodiments, the reactive group $Y^1$ of the organo-trifluoroborate compound of general formula EII is alcohol. In a preferred embodiment, $Y^1$ is alkoxy. In another preferred embodiment, $Y^1$ is —OCH$_3$.

In some embodiments, when the Y1 is —OCH$_3$, the linker (L) of the organo-trifluoroborate compound of general formula EII is —(CH$_2$CH$_2$O)$_{1-36}$—CH$_2$—; In a preferred embodiment, L is —(CH$_2$CH$_2$O)$_3$—CH$_2$—. In another preferred embodiment, L is —(CH$_2$CH$_2$O)$_7$—CH$_2$—. In another preferred embodiment, L is —(CH$_2$CH$_2$O)$_{15}$—CH$_2$—, or —(CH$_2$CH$_2$O)$_{23}$—CH$_2$—.

In some embodiments, the organo-trifluoroborate compound of general formula EII can be the following compounds.

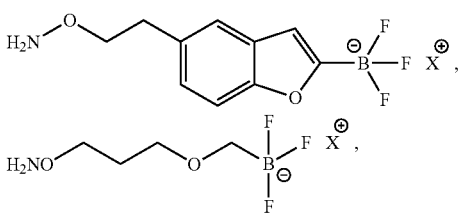

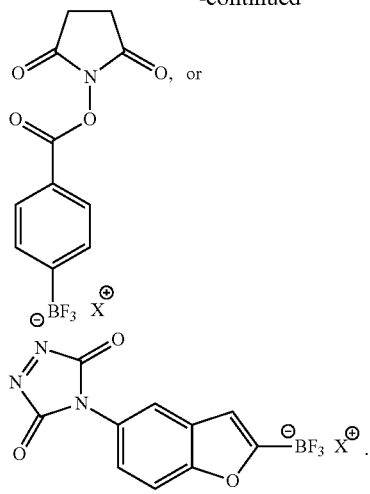

In some embodiments, $X^\oplus$ is a positively charged counter ion selected from the group consisting of K$^+$, Cs$^+$, Rb$^+$, quaternary ammonium, pyridinium, pyrazolium, thiazolium, morpholium, triazolium, imidazolium, bezoxazolium, thiadiazolium, oxadiazolium, and guanidinium ions. In a preferred embodiment, $X^\oplus$ is K$^+$.

In yet another aspect, the invention generally relates to a an organo-bis-trifluoroborate compound having structural formula AII.

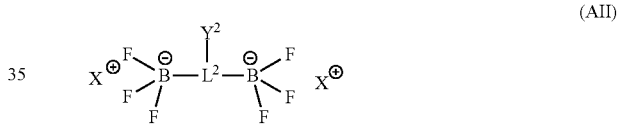

(AII)

wherein $Y^2$ is a functional group selected from the group consisting of an alcohol, alkoxy, aryloxy, diene, dienophile, carboxylic acid, amine, thiol, alkyl halide, ketone, aldehyde, aminooxy, hydrazine and its derivatives, activated ester, acid halide, isocyanate or thio-isocyanate, azo, alkyne, 1,3-dipolariphile, sulfonyl chloride, glyoxal, epoxide or oxirane, carbonate, aryl halide such as fluorobenzene derivatives, imidoester or imidate, anhydride, fluorophenyl ester, hydroxymethyl phosphine derivative, maleimide, aziridine, acryloyl derivative, arylating agent such as derivatives of benzene that possess either halogen or sulfonate groups on the ring, thiol-disulfide exchange reagent such as pyridyldithiol and thiolnitrobenzoic acid, or vinylsulfone group;

$L^2$ is a linker or a combination of 2 to 4 linkers that independently selected from the group consisting of C$_1$-C$_{20}$ alkyl, —(CH$_2$CH$_2$O)$_{1-36}$—, —(CH$_2$CH$_2$O)$_{1-36}$—CH$_2$—, a peptide, a peptidomimetic oligomer, alicyclyl, optionally substituted alicyclyl, heteroalicyclyl, optionally substituted heteroalicyclyl, optionally substituted aryl.

$X^\oplus$ is any positively charged counter ion.

In some embodiments, the organo-bis-trifluoroborate compound of general formula AII is labeled with one or more stable heavy isotopes selected from $^{10}$B and $^{11}$B, $^{12}$C and $^{13}$C, $^{14}$N and $^{15}$N, $^{16}$O and $^{18}$O, $^1$H and $^2$H isotopes at select atomic sites such that the total additional mass due to heavy isotope labeling is distributed between the reactive group, the linker, and trifluoroborate group to produce a set of isobaric and mass differential tags.

In some preferred embodiments, $Y^1$ of the bis-organo-trifluoroborate compound of the general formula AII is an aldehyde and ketone reactive aminooxy (—$ONH_2$) group.

In some embodiments, the bis-organo-trifluoroborate compound of the general formula AII has a specific chemical structure (AIII).

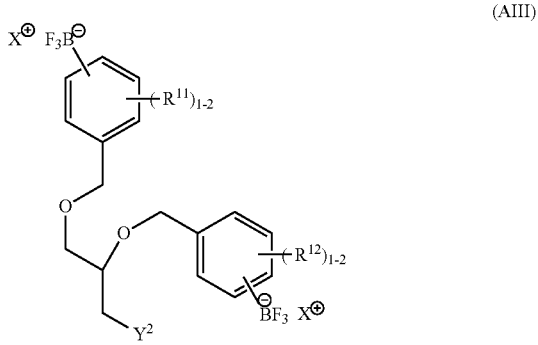

(AIII)

wherein $R^{11}$ and $R^{12}$ is independently selected from a group consisting H and alkoxy.

In some preferred embodiments, $Y^1$ of the organo-trifluoroborate compound of the general formula AIII is an aldehyde or ketone reactive aminooxy (—$ONH_2$) group. In another preferred embodiment, $Y^1$ is an acid reactive amine group. In another preferred embodiment, when $Y^1$ is an aminooxy or amine group, each of $R^{11}$ and $R^{12}$ can be H.

In some embodiments, the organo-trifluoroborate compound of general formula AII is the following compound:

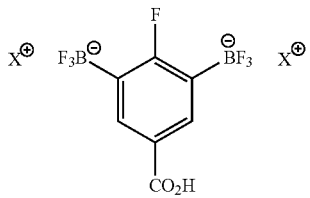

In some embodiments, $X^{\oplus}$ is a positively charged counter ion selected from the group consisting of $K^+$, $Cs^+$, $Rb^+$, quaternary ammonium, pyridinium, pyrazolium, thiazolium, morpholium, triazolium, imidazolium, bezoxazolium, thiadiazolium, oxadiazolium, and guanidinium ions. In a preferred embodiment, $X^{\oplus}$ is $K^+$.

In yet another aspect, the invention generally relates to methods wherein the analyte of interest in high-resolution negative ion mode can be identified and characterized through an accurate determination of the mass of the organo-trifluoroborate or organo-multi-trifluoroborate-tagged analyte.

In yet another aspect, the invention generally relates to a composition wherein a mixture of organo-trifluoroborate or organo-multi-trifluoroborate tags in suitable proportions is used as a calibration mixture for mass spectrometers in negative ion mode. In some embodiments, enriched boron isotopes are used in the mixture.

In some cases, a set of calibrators is prepared using known concentrations of analytes and its labeled internal standard (IS). Labels in IS can be of many types. In some embodiments, labeled IS are deuterated ($^2H$) analytes. In some other embodiments, labeled IS are independently $^{13}C$, $^{15}N$, $^{10}B$, or $^{11}B$-enriched analytes. In some embodiments, labeled IS are a combination of all of the above. In some embodiments, such calibrators are spiked into analyte-depleted samples to generate a set of calibrators. Such calibrators are used to generate a calibration curve, which includes concentration vs. mass spectrometric response factors. From the calibration curve, the concentration of the analyte in unknown samples can be determined.

In yet another aspect, the invention generally relates to a kit comprising organo-trifluoroborate or organo-multi-trifluoroborate mass tags, calibrates, internal standards, biological matrices and standards, solvents, tubes and vials, separation media, capture media or agents, enrichment media or reagents, precipitating reagents, salts and buffers, system qualifying solutions, quality control samples, pH adjusting and other necessary reagents, racks and manifolds, with directions and handouts included.

In some embodiments, such a kit can be used to identify and quantify analytes or markers in single or multiplexed fashion in negative ion mode.

In yet another aspect, the invention generally relates to a liquid chromatography method to separate the trifluoroborate-tagged analytes and the detection and fragmentation of those analytes by a mass spectrometer.

In yet another aspect, the invention generally relates to a synthetic process or processes for organo-borate compounds or organo-borate mass tags having general formula E or formula A.

In yet another aspect, the invention generally relates to a synthetic process or processes for boron isotope ($^{11}B$ or $^{10}B$) enriched organo-trifluoroborate or organo-multi-trifluoroborate mass tags having general formula E or formula A.

In some embodiments, the sample is processed to enrich the analyte present in the sample. Sample processing can be done using various methods, including but not limited to protein precipitation, solid phase extraction, liquid-liquid extraction, solid liquid extraction, ultracentrifugation, protein removal by molecular weight cut-off membranes, protein removal by filtration through hollow fiber, gel electrophoresis, and purification by various medias such as silica gel, Celite®, reversed phase silica, and hydrophilic silica. Analytes in the samples can be enriched by affinity purification. Non-limiting examples include antibody, chelators, affinity tags, and reversible binders/releasers.

In some embodiments, an artificial analyte-depleted matrix or sample can be generated by dissolving standard highly abundant proteins such as bovine serum albumin (BSA) or human serum albumin (HSA) in aqueous buffers.

In some embodiments, the processed samples including analytes and IS are reacted with organo-trifluoroborate reagents and analyzed by LC-MS/MS.

In yet another aspect, the invention generally relates to a method for analyzing an analyte, the method includes: covalently bonding a mass tag comprising an organo-trifluoroborate moiety to an analyte to form a tagged analyte; subjecting the tagged analyte to mass spectroscopic fragmentation in negative ion mode under conditions to produce negatively charged fragment ions and molecules with no charge (neutral losses); and qualitatively or quantitatively identify the analyte based on the mass spectrum.

In certain embodiments, the method further includes subjecting the tagged analyte to chromatographic separation before mass spectroscopic fragmentation.

In yet another aspect, the invention generally related to a kit that includes a mass tag comprising an organo-trifluoroborate moiety suitable for tagging an analyte so as to, under conditions of mass spectroscopic fragmentation in negative ion mode, produce negatively charged fragment ions and molecules with no charge (neutral losses), thereby providing qualitatively or quantitatively identification of the analyte based on the mass spectrum.

The foregoing aspects and embodiments of the invention may be more fully understood with reference to the following figures, detailed description, and claims.

DEFINITIONS

Definitions of specific functional groups and chemical terms are described in more detail below. General principles of organic chemistry, as well as specific functional moieties and reactivity, are described in "Organic Chemistry", Thomas Sorrell, University Science Books, Sausalito: 1999.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Sambrook et al., Molecular Cloning: A Laboratory Manual, 2nd Edition (Cold Spring Harbor Laboratory, 1989); and the like. Still, certain terms are defined below for the sake of clarity and ease of reference.

General terminologies of mass spectroscopy including accurate mass and high resolution mass (HRMS) used herein can be found from IUPAC's publication (Murray, K. K. et. al. Pure Appl. Chem., Vol. 85, No. 7, pp. 1515-1609, 2013).

The terms "mass tags", "labels", and "labeling reagent", as used herein, refer to molecules, groups or moieties that can assist in mass spectrometric analysis. These terms can be used interchangeably.

The term "mass", as used herein, refers to the molecular mass or monoisotopic mass, that is, the mass of the molecule having only the most common isotope of each element.

As described here, the mass of an atom or molecules sometimes can be rounded to the nearest whole number atomic mass unit (amu), or to the nearest tenth or hundredth of an amu. Sometimes the mass of an atom or molecule may be expressed by its approximate mass within a range so that if isotopes of different atoms are interchanged in between the molecules, the difference in the mass of such molecules will be negligible. For example, if one wants to create a mass difference of one unit (1 amu) between two chemically similar molecules, either a $^{14}N$ atom can be replaced with an $^{15}N$ atom or a $^{12}C$ atom can be replaced with a $^{13}C$ atom and the mass difference between $^{12}C \rightarrow ^{13}C$ and $^{14}N \rightarrow ^{15}N$ will only be 0.00632 amu. Similarly, a mass difference of 2 amu can be achieved by substituting two $^{12}C$ atoms with two $^{13}C$ atoms or one $^{13}C$ atom and one $^{15}N$ atom or one $^{18}O$ atom, provided the molecule has C, N, and O atoms.

The term "accurate mass", as used herein, refers to the experimentally determined mass of an ion that is used to determine an elemental formula.

The term "fragmentation", as used herein, refers to: collision induced dissociation (CID), collision activated dissociation (CAD), photo induced dissociation (PID), surface induced dissociation (SID), electron induced dissociation (ECD), post source decay (PSD), a combination thereof, or any other similar techniques that induce bond dissociation in molecules or fragments thereof.

The terms "parent ion" and "precursor ion", as used herein, interchangeably, refer to an ion that reacts to form particular product ions. The reaction can be unimolecular dissociation, ion/molecule reaction, isomerization, or a change in charge state.

The terms "product ion", "daughter ion", and "fragment ion", as used herein, interchangeably, refer to an ion formed as the product of a reaction involving a particular precursor ion. The reaction can be unimolecular dissociation, an ion/molecule reaction, or simply involve a change in the number of charges.

The term "product ion scan", as used herein, refers to an MS/MS experiment that records all product ions derived from a single parent ion.

The term "diagnostic ion", as used herein refers, to a product ion whose formation reveals structural or compositional information about its precursor.

The term "total ion current (TIC)", as used in diagrams here, refer to the sum of all of the separate ion currents carried by the different ions contributing to the spectrum.

The terms "mass differential tags", "mass differential labels", and "mass differential labeling reagent", as used herein, interchangeably, refer to, for example, a set molecules with significant structural and chemical similarities but different masses because of the difference in isotopic enrichment at various atomic positions among the members of the set. When subject to fragmentation, each member of the set can produce a daughter ion of different mass. These characteristic daughter ions can also be referred to as "Flag ions".

The terms "isobaric tags", "isobaric labels", and "isobaric labeling reagent", as used herein, interchangeably, refer to, for example, a set molecules that have significant structural and chemical similarities and very similar masses because of the difference in isotopic enrichment at various atomic positions among the members of the set. When subject to fragmentation, each member of the set can produce a daughter ion of different mass. These characteristic daughter ions can also be referred to as "Flag ions".

The term "alkyl", as used herein, refers to a branched, unbranched, or cyclic hydrocarbon having, for example, from about 1 to about 20 carbon atoms, and preferably from about 1 to about 12, from about 1 to about 6, or from about 1 to about 4 carbon atoms. Examples include, but are not limited to, methyl; ethyl; 1-propyl; 2-propyl; 1-butyl; 2-methyl–1-propyl; 2-butyl; 2-methyl-2-propyl (t-butyl); 1-pentyl; 2-pentyl; 3-pentyl; 2-methyl-2-butyl; 3-methyl-2-butyl; 3-methyl-1-butyl; 2-methyl-1-butyl; 1-hexyl; 2-hexyl; 3-hexyl; 2-methyl-2-pentyl; 3-methyl-2-pentyl; 4-methyl-2-pentyl; 3-methyl-3-pentyl; 2-methyl-3-pentyl; 2,3-dimethyl-2-butyl; 3,3-dimethyl-2-butyl; hexyl; octyl; decyl; dodecyl; and the like. The alkyl can be unsubstituted or substituted. The alkyl can also be, optionally, partially or fully unsaturated. As such, the use of an alkyl group includes both alkenyl and alkynyl groups.

The term "reactive group", as used herein, refers to alcohol, alkoxy, aryloxy, diene, dienophile, carboxylic acid, amine, thiol, alkyl halide, ketone, aldehyde, aminooxy, hydrazine and its derivatives, activated ester, acid halide, isocyanate or thio-isocyanate, azo, alkyne, 1,3-dipolariphile, sulfonyl chloride, glyoxals, epoxide or oxirane, carbonate, aryl halide such as fluorobenzene derivatives, imidoester or imidate, anhydride, fluorophenyl ester, hydroxymethyl phosphine derivative, maleimide, aziridine, acryloyl derivative, arylating agent such as derivatives of benzene that possess either halogen or sulfonate groups on the ring, thiol-disulfide exchange reagent such as pyridyldithiol and thiolnitrobenzoic acid, or vinylsulfone groups.

The term "analyte", as used herein, refers to steroids, hormones, peptides and proteins, protein fragments, antibodies, vitamins, prostaglandins, fatty acids, carbohydrates, small molecule metabolites, biomarkers, amino acids, nucleotides, nucleosides, DNA, RNA, lipids, or enzymes. Also, an analyte can be a conjugate (homogeneous or heterogeneous) of the above-mentioned analytes. Also, an analyte can be synthetic or semisynthetic molecules, drug candidates, metabolite intermediates, modified metabolites and their intermediates, non-natural amino acids, DNA, RNA analogs, peptide nucleic acids (PNA), chimeric molecules, or biodegradation products.

The term "sample", as described herein, refers to preserved, treated, or untreated, human or animal serum, plasma, blood, urine, cerebral fluid, tissue, hair, fur, skin, bone, bone marrow, saliva, excretions, body fluids, nails, teeth, cells, cell culture media, protein digest, biosynthesis media, DNA or RNA extracts, forensic specimens, autopsy samples, biopsy samples, food and beverages, food-related products, animal food, animal byproducts, agricultural products, fertilizers, bacterial culture media, tissue culture media, dyes and fabrics, paint and varnishes, construction material, mining and petroleum industry products or byproducts and environmental samples, genetically modified crops and related products, or cloned animals organisms and related products.

The term "molecular weight ladder" or "molecular weight (MW) marker", as used herein, interchangeably, refers to a mixture of similar or different molecules of different molecular weights. Molecules are chosen for the lowest and highest MW components on the scale or ladder, with the other components spanning the in-between MWs. Spacing of the MWs depends on the actual application. MW spacing of the scale or ladder can be gradual, evenly spaced, or condensed in one or more than one section.

The term "internal standard (IS)", as used herein, refers to a compound purposely added to both samples and/or standards at a known concentration to provide a basis for comparison in quantitation.

The term "organo-trifluoroborate", as used herein, refers to an organic compound that includes one or more anions with the general formula $[RBF^3]^-$ wherein R refers to any organic compound. Examples of potassium organo-trifluoroborates can be found in this review paper (Darses, S.; Genet, J. Chem. Rev. 2008, 108, 288-325).

The term "linker", as used herein, refers to groups or bonds that are normally formed as the result of a chemical reaction and typically with covalent bond(s). A linker may include one or more different linkers. A linker may include one or more extra spacers, such as ethylene glycol, propylene glycol, methylene, a peptide, or a peptidomimetic oligomer. Linkers include, for example, substituted or un-substituted heteroalicyclyl $C_1$-$C_{12}$ alkyl, —$(CH_2CH_2O)_{1\text{-}36}$—, —$(CH_2CH_2O)_{1\text{-}36}$—$CH_2$—, substituted or un-substituted alicyclyl, heteroalicyclyl, optionally substituted aryl, peptides, and peptidomimetic oligomers. The linkers may include one or more linking groups, such as acyl-based linking groups (e.g., —C(O)—NH— and —OC(O)NH—). Exemplary linking groups include, but are not limited to, —C(=$G^2$)-$G^1$-, -$G^1$-C(=$G^2$)-, -$G^3$-, -$G^1$-C(=$G^2$)-$G^1$-, —S—S—, —S—$(CH_2)_2$—S$(O)_2$—, —S$(O)_2$—$(CH_2)_2$—S—, —S$(O)_2$—N($R^3$)—, —N($R^3$)—S$(O)_2$—, —C(O)—NH—NH—$CH_2$—, —C(O)—NH—N=CH—, —CH=N—NH—C(O)—, —$CH_2$—NH—NH—C(O)—, —N($R^3$)—S$(O)_2$—N($R^3$)—, —C(O)—NH—CH($CH_2$SH)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=$NH_2^+$)—NH—, —NH—C(=$NH_2^+$)—, —O—P(=O)($O^-$)—NH—, —NH—P(=O)($O^-$)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, —O—P(=S)($S^-$)—O—,

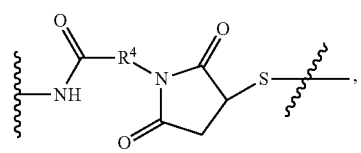

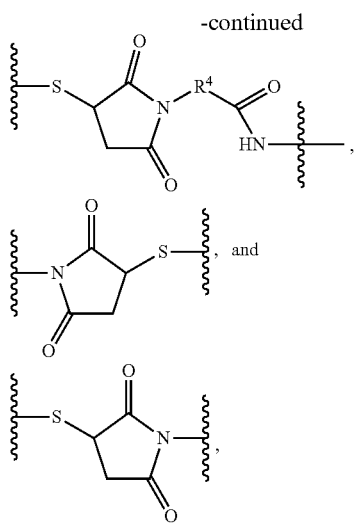

wherein each $G^1$ is independently selected from $NR^3$, O, and S; each $G^2$ is independently O or S; each $G^3$ is independently selected from S, O, $NR^3$, and $SO_2$; each $G^4$ is independently O or $NR^3$; each $R^3$ is independently selected from hydrogen, $C_1$-$C_8$ alkyl, —$(OCH_2CH_2)_{1-3}$, optionally substituted alicyclyl, and optionally substituted heteroalicyclyl; each $R^4$ is independently $C_1$-$C_8$ alkyl, —$(OCH_2CH_2)_{1-3}$, optionally substituted alicyclyl, and optionally substituted heteroalicyclyl.

BRIEF DESCRIPTION OF THE FIGURES

FIG. 1 illustrates the fragmentation pathways of organo-trifluoroborates.

FIG. 2 illustrates predictable fragmentation pathways of two organo-trifluoroborates.

FIG. 3 illustrates a collisional energy (CE) scan of potassium benzofuran-2-trifluoroborate. Fragmentation at CE=−45 ev shows the predictable fragment with $BF_3$ as a neutral loss.

FIG. 4 illustrates a collisional energy (CE) scan of potassium trans-styryltrifluoroborate. Fragmentation at CE=−45, −30, and −15 ev shows the predictable fragments with HF and CH=$CHBF_3$ as neutral losses.

FIG. 5 illustrates the fragmentation pathways of organo-bis-trifluoroborates.

FIG. 6 illustrates low to high mass parent-daughter ion monitoring in negative ion mode.

FIG. 7 illustrates trifluoroborate-containing mass tags.

FIG. 8 is a schematic example of a reaction of a ketone-reactive trifluoroborate mass tag with a ketone analyte and fragmentation of the tagged analyte in a mass spectrometer.

FIG. 9 is a schematic example of a reaction of an amine-reactive trifluoroborate mass tag with an amine analyte and fragmentation of the tagged analyte in a mass spectrometer.

FIG. 10 is a description of ketone-reactive mass-differential trifluoroborate mass tags. Such a mass tag is reacted with a ketone analyte from two different samples. After derivatization with the mass tags, samples are mixed and analyzed by LC-MS/MS. Because of the difference in the mass of parent-daughter ions, multiple (in this case two) samples can be analyzed in one LC-MS/MS run, increasing the throughput of analysis.

FIG. 11 is Q1-MS scan (low resolution) of a mixture of compound 23, 24, 25 and 26 infused directly in mass spectrometer as methanol-water solution.

FIG. 13 is MS/MS fragmentation of compound 2 forming predictable fragments.

FIG. 14 shows isotopic distribution of compound 2 showing presence of $^{10}B$ and $^{11}B$.

DETAILED DESCRIPTION OF THE INVENTION

Figure 12:
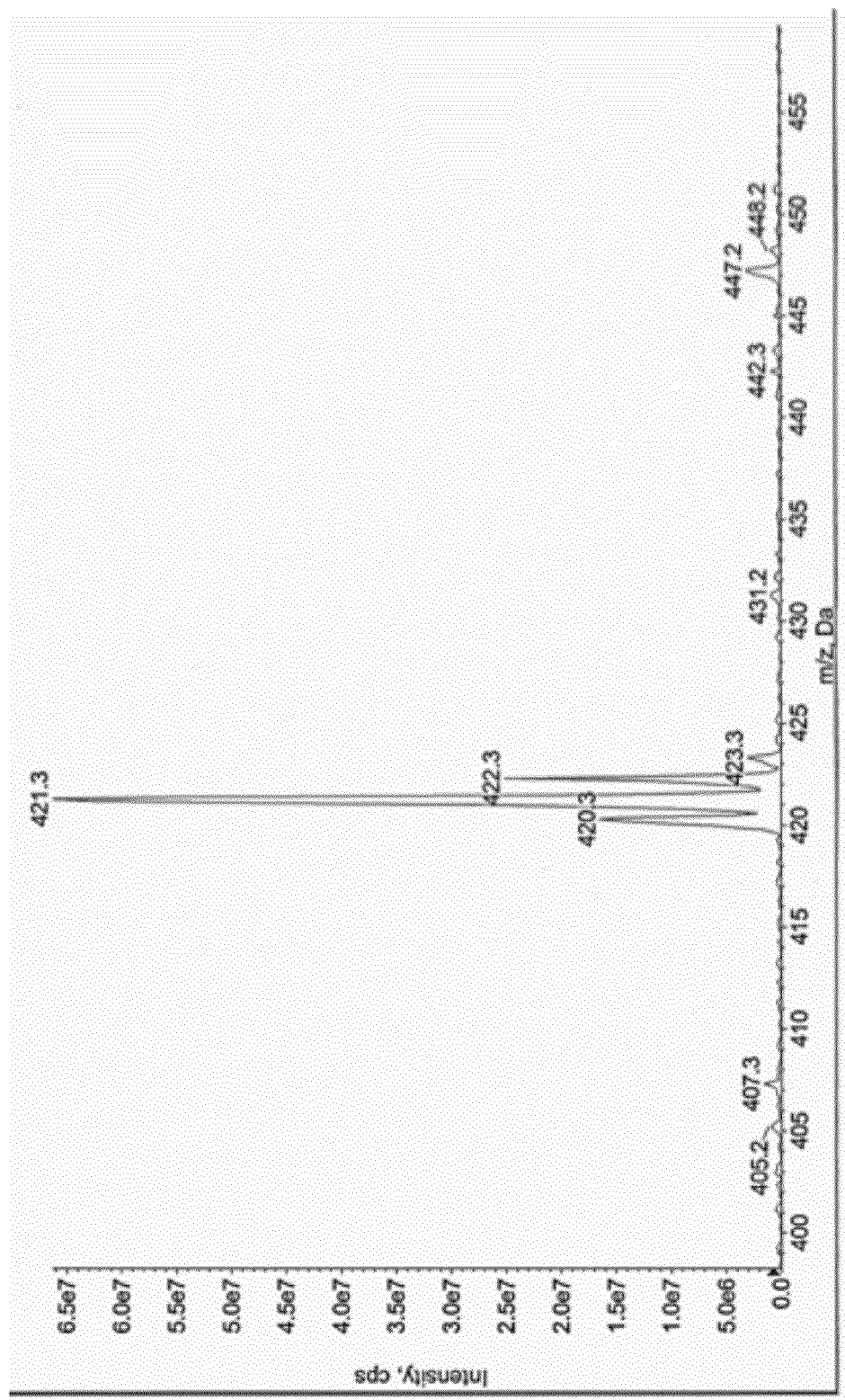
FIG. 12 shows Q1-MS scan (low resolution) of a mixture of compound 23, 24, 25 and 26 infused directly as methanol-water solution. Contributions of $^{10}B$ isotope are seen as a peak at 1 amu less left to the major isotopic peak containing $^{11}B$ isotope.
Figure 12:
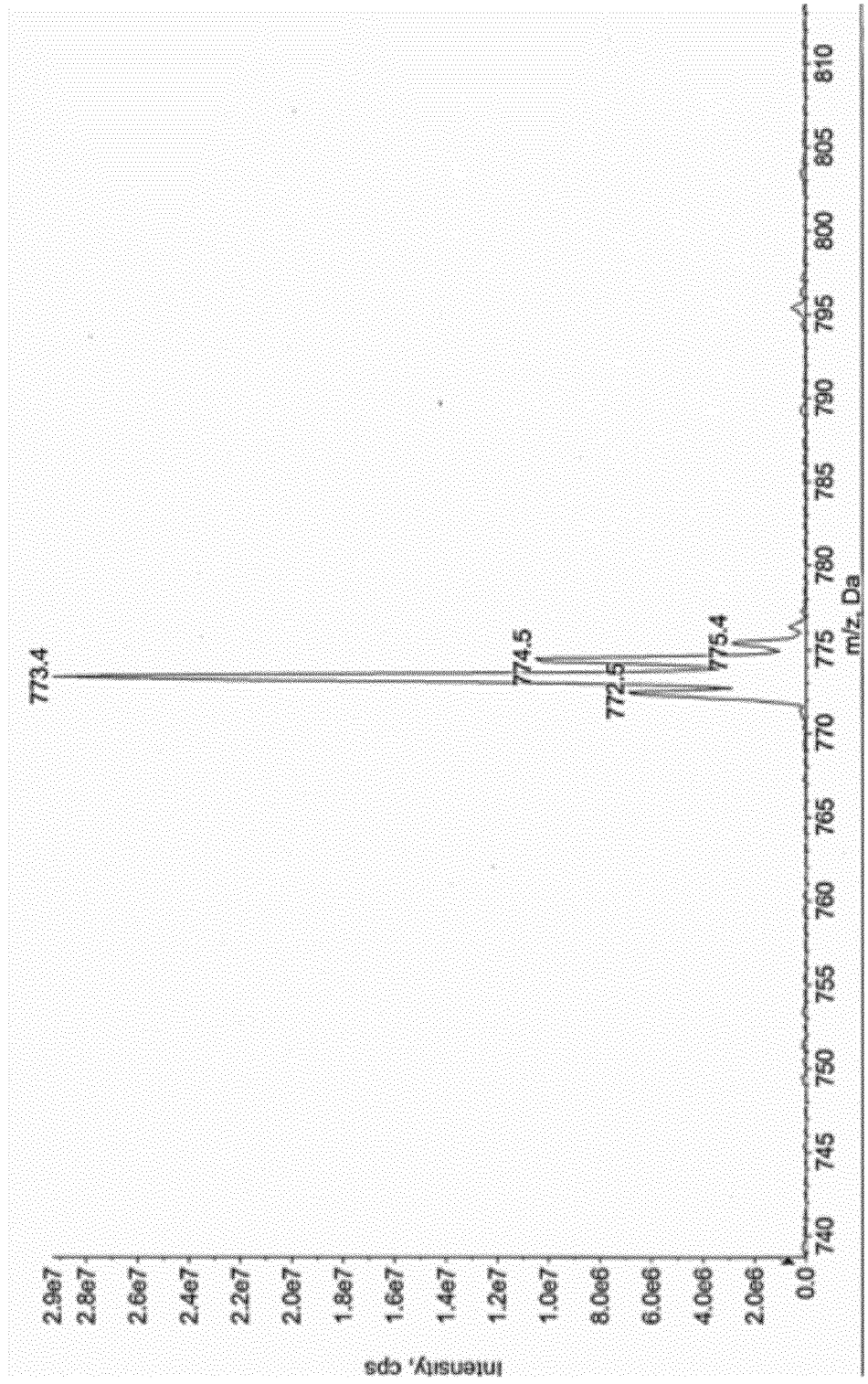

Organo-trifluoroborates offer a niche in organic synthesis because of their use and versatility in Suzuki coupling (Darses, S., Genet, J. Chem. Rev. 2008, 108, 288-325). As a consequence of the success of Suzuki reactions, a wide variety of commercially available organo-trifluoroborates are at the disposal of organic chemists. Because of the formal negative charge on the trifluoroborate group, organo-trifluoroborates can be readily detected with enhanced sensitivity in negative ion mode mass spectrometric analysis (Petrillo, D. E. et. al. J. Am. Chem. Soc. 2007, 18, 404-405). The formal negative charge on organo-trifluoroborates is not affected by the pH of the media and such compounds are stable under ambient conditions and in the presence of water. Unlike borates, organo-trifluoroborates remain as monomeric species at any practical concentration range, making mass spectrometric analysis less complicated.

Organo-trifluoroborates, when subjected to fragmentation in a mass spectrometer, such as collision induced dissociation (CID), were discovered by us, preferentially undergo neutral losses of hydrogen fluoride (HF) or boron trifluoride ($BF_3$), transferring the negative charge to the rest of the fragment molecule (FIG. 1).

This phenomenon of neutral loss and negative charge transfer opens up new space for predictable parent-daughter ion monitoring and analysis of tagged molecules in $MS^2$ or $MS^3$ negative ion mode, in general in $MS^n$ negative ion mode. Such phenomena can be coupled with liquid chromatography to enable LC-$MS^n$ monitoring in negative ion mode. For example, an organo-trifluoroborate tag with aminooxy or active ester functionality can selectively react with ketone or amine analytes. Upon reaction, the tagged molecule bears a negative charge. The negatively charged tagged analyte can then be fragmented in a mass spectrometer with optimized collisional energy to generate specific product ion(s) that provide structural information about the analyte. Thus, detection of tagged analytes can be performed selectively and at high sensitivities. If a heavy isotope-labeled internal standard of the analyte is available and can be spiked in the sample at a known concentration before the tagging reaction, absolute quantitation of the analyte can be achieved by comparing the area ratio of internal standard to analyte.

One of the limitations of LC-MS/MS analysis is the time and sequential mode of analysis, which even at approximately 5 minutes per sample can lead to a considerable amount of time in a clinical setting when one typically needs to analyze a high volume of samples. Other methods of analysis, such as ELISA, can be performed or read in parallel, significantly reducing the analysis time. Although ELSA is not as specific and precise as LS-MS/MS based assays, many laboratories choose to use ELISA because of its high-throughput.

To increase the throughput of analysis in LC-MS-based assays, multiple reagents with different heavy atom-labeled mass tags are commonly used. Organo-trifluoroborates can also be labeled at specific positions within the molecule with heavy stable isotopes, including but not limited to $^{10}$B and $^{11}$B, $^{12}$C and $^{13}$C, $^{14}$N and $^{15}$N, $^{16}$O and $^{18}$O, $^{1}$H and $^{2}$H isotopes, or a combination of these isotopes, to generate a set of isobaric or mass differential tags or reagents. Such a set of reagents can be used in a multiplexed format to speed up analysis. Such a set of reagents can be used for absolute and relative quantitation of analytes in negative ion mode. Such a set of reagents can be used for absolute and relative quantitation of analytes in a multiplexed format in negative ion mode.

Another way to speed up LC-MS/MS based assays is to use a multiplex LC system in front of a mass spectrometer. If multiplex reagents can be used in conjugation with a multiplex LC system for LC-MS/MS analysis, the throughput of analysis can be increased dramatically to meet the need of clinical labs where the analysis of more than 1000 samples per day for a specific analyte is a common requirement.

The negatively charged fragment formed upon collisionally induced dissociation of organo-trifluoroborate and neutral loss of hydrogen fluoride (HF) or boron trifluoride (BF$_3$) are also discovered by us that can be further fragmented in MS$^3$ mode to generate smaller, predictable, negatively charged molecular fragments. Such a fragmentation pathway is directed by the kinetic or thermodynamic stability of the fragmentation product (FIGS. 2, 3, & 4).

In general, very few structure-specific (fragments having structural information about the analyte) fragments are formed. Such structure-specific fragments can be used for quantitative or qualitative MS$^n$ transition monitoring. For example, MS and MS/MS analysis of compound 2 (Example 1, FIGS. 13 & 14) demonstrated the characteristic isotopic pattern of trifluoroborate tags and its predictable fragmentation patterns. Because of the discriminatory nature of the fragmentation pathway, fewer ions are produced, funneling most of the ion currents to a handful of ions. Such limited distribution or funneling of ion current leads to intense MS$^n$ transitions and, thus, enhanced sensitivity in negative ion MS$^n$-based detection. Analyzing biological samples for a specific analyte, even by a targeted LC-MS/MS method, can be challenging. A very low concentration of the analyte, sometimes in the range of low picogram/mL to low femtogram/mL of sample, is common. Also, the presence of structurally similar (stereo and geometric isomers) isobaric analytes in the sample can pose significant interference problems.

One way to overcome this problem is to use higher order MS fragmentation. In general, the MS$^3$ mode of analysis is more specific than the MS$^2$ mode of analysis and can filter out interfering molecules. Because of the predictable nature of the higher order fragmentation of organo-trifluoroborate analysis by MS$^3$ (or MS$^4$) mode, the use of organo-trifluoroborate tags can provide avenues for detecting and quantifying analytes present in very small quantities and in different isoforms in biological samples.

In some cases, two trifluoroborate moieties may be attached to the same tag or reagent. In such a case the organo-bis-trifluoroborate are doubly negative charged and the observed mass (m/z, mass over charge) in the negative mode are half of the actual mass of the molecule. If such a molecule is fragmented by collisional energy, it produces a primary fragment ion (daughter ion 1) bearing a double negative charge by eliminating HF or BF$_3$ (e.g., FIG. 5). If sufficient collision energy is applied, daughter ion 1 fragments further to produce mono-negative structure-specific daughter ion(s) 2 (e.g., FIG. 6). Such transitions can be designated as MS$^3$ or MS$^2$ transitions, depending on how one monitors such fragmentation. In such cases, one observes a lower mass/charge (m/z) to higher m/z parent-daughter ion transition (e.g., FIG. 6). Such transitions are unique in the sense that they carry far less background noise. LC parent-daughter ion monitoring (or analysis) is substantially noise-free, allowing enhanced detection limits for the analytes tagged with such organo-bis-trifluoroborate mass tags. Mass tags are preferably designed taking into consideration the thermodynamics and kinetics of the dissociation of the neutral fragment losses from the molecule so that the desired low to high mass transition can be tuned to produce the desired noise reduction.

In some embodiment, the organo-trifluoroborate or organo-bis-trifluoroborate tag may be connected to a reactive group via a linker, spacer, bond, or part of another molecule. The reactive group is designed to react specifically with the analyte of interest, depending on the functional group(s) present in the analyte. The reactive group can be chosen from alcohol, alkoxy, aryloxy, diene, dienophile, carboxylic acid, amine, thiol, alkyl halide, ketone, aldehyde, aminooxy, hydrazine and its derivatives, activated ester, acid halide, isocyanate or thio-isocyanate, azo, alkyne, 1,3-dipolariphile, sulfonyl chloride, glyoxal, epoxide or oxirane, carbonate, aryl halide such as fluorobenzene derivatives, imidoester or imidate, anhydride, fluorophenyl ester, hydroxymethyl phosphine derivative, maleimide, aziridine, acryloyl derivative, arylating agent such as derivatives of benzene that possess either halogen or sulfonate groups on the ring, thiol-disulfide exchange reagent such as pyridyldithiol and thiolnitrobenzoic acid, or a vinylsulfone group. The trifluoroborate group of the tag is chemically stable and does not react with any other reactive groups mentioned above. Such chemical stability and compatibility enable syntheses of various organo-trifluoroborate mass tags for different applications without the risk of self-reactivity of the mass-tag and reduced shelf life.

For example, organo-trifluoroborate compound or mass tag having the general formula (EI) can be designed for negative ion mass-spectrometric application. In formula E1, Y is a reactive group. L is a bond, a linker, or a combination of several linkers. X$^\oplus$ is a positively charged counter ion.

(EI)

In another example, organo-bis-trifluoroborate compound or mass tag having the general formula AI can be designed for negative ion mass-spectrometric application. In formula AI, Y is a reactive group. L is a bond, a linker, or a combination of several linkers. X$^\oplus$ is a positively charged counter ion.

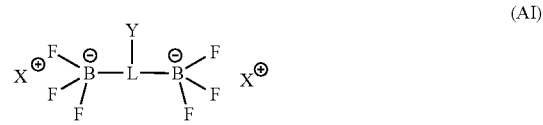

(AI)

Linker can include one or several spacer that independently selected from the group consisting of ethylene glycol, propylene glycol, methylene, a peptide, a peptidomimetic oligomer, substituted or un-substituted heteroalicyclyl C$_1$-C$_{12}$ alkyl, —(CH$_2$CH$_2$O)$_{1-36}$—, —(CH$_2$CH$_2$O)$_{1-36}$—CH$_2$—, substituted or un-substituted alicyclyl, heteroalicyclyl, and substituted or un-substituted aryl. Linker can also include one or several linking groups that independently selected from the group consisting of —C(=G²)-G¹, -G¹-C(=G²)-, -G³, -G¹-C(=G²)-G¹-, —S—S—, —S—(CH₂)₂—S(O)₂—, —S(O)₂—(CH₂)₂—S—, —S(O)₂—N(R³)—, —N(R³)—S(O)₂—, —C(O)—NH—NH—CH₂—, —C(O)—NH—N=CH—, —CH=N—NH—C(O)—, —CH₂—NH—NH—C(O)—, —N(R³)—S(O)₂—N(R³)—, —C(O)—NH—CH(CH₂SH)—, —N=CH—, —NH—CH₂—, —NH—C(O)—CH₂—C(O)—NH—, —CH=N-G⁴-, —CH₂—NH-G⁴-, -G⁴-NH—CH₂—, -G⁴-N=CH—, —C(=NH₂⁺)—NH—, —NH—C(=NH₂⁺)—, —O—P(=O)(O⁻)—NH—, —NH—P(=O)(O⁻)—O—, —CH₂—CH(NH₂)—CH₂—S—, —S—CH₂—CH(NH₂)—CH₂—, —O—P(=O)(O⁻)—O—, —O—P(=O)(S⁻)—O—, —O—P(=S)(S⁻)—O—,

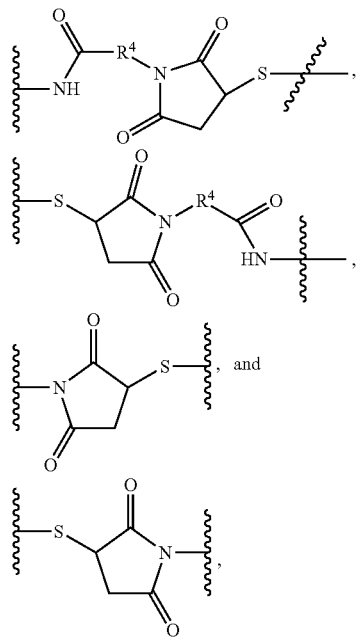

wherein each G¹ is independently selected from NR³, O, and S; each G² is independently O or S; each G³ is independently selected from S, O, NR³, and SO₂; each G⁴ is independently O or NR³; each R³ is independently selected from hydrogen, C₁-C₈ alkyl, —(OCH₂CH₂)₁₋₃, optionally substituted alicyclyl, and optionally substituted heteroalicyclyl; each R⁴ is independently C₁-C₈ alkyl, —(OCH₂CH₂)₁₋₃, optionally substituted alicyclyl, and optionally substituted heteroalicyclyl.

$X^{\oplus}$ is a positively charged counter ion such as K⁺, Cs⁺, Rb⁺, quaternary ammonium, pyridinium, pyrazolium, thiazolium, morpholium, triazolium, imidazolium, bezoxazolium, thiadiazolium, oxadiazolium and guanidinium ions.

More specific organo-trifluoroborate can be designed for negative ion mass-spectrometric application:

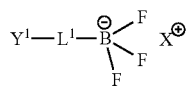 (EII)

wherein $Y^1$ is a reactive group selected from the group consisting of alcohol, alkoxy, a diene, dienophile, aminooxy, activated ester, N-hydroxysuccinimide ester, alkyl halide, aryl halide, maleimide, thiol-disulfide exchange reagent such as pyridyldithiol and thiolnitrobenzoic acid, or vinylsulfone group;

$L^1$ is a linker or a combination of 2 to 4 linkers that individually selected from the group consisting of C₁-C₂₀ alkyl, —(CH₂CH₂O)₁₋₃₆—, —(CH₂CH₂O)₁₋₃₆—CH₂—, a peptide, a peptidomimetic oligomer, alicyclyl, optionally substituted alicyclyl, heteroalicyclyl, optionally substituted heteroalicyclyl, optionally substituted aryl; and $X^{\oplus}$ is a positively charged counter ion.

$Y^1$ of the organo-trifluoroborate compound of the general formula E11 can be an aldehyde/ketone reactive aminooxy (—ONH₂) group or an amine reactive N-hydroxysuccinimide ester group. In some cases, $Y^1$ is a diene reactive group having the following structural formula:

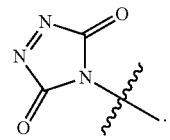

In some cases, linker (L) of the organo-trifluoroborate compound of the general formula EII has a benzofuran core structure with the following structural formula, wherein n is 0 or an integer selected from 1 to about 12.

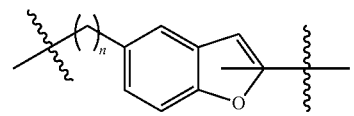

In some cases, the linker can be an ethylene glycol linker (—(CH₂CH₂O)₁₋₃₆—CH₂—) and $Y^1$ is an alcohol or alkoxy. Such compounds can be used either alone or as a mixture for calibrating the mass spectrometry in negative mode mass application. Example 9 illustrates the synthesis of such compounds and their application for negative mode mass analysis.

Few examples of organo-trifluoroborate compounds of general formula EII are illustrated in this application.

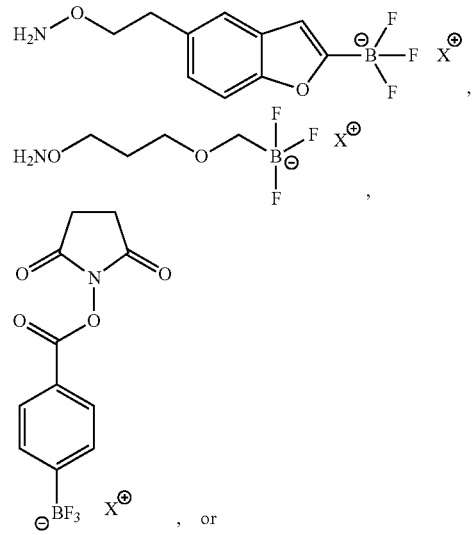

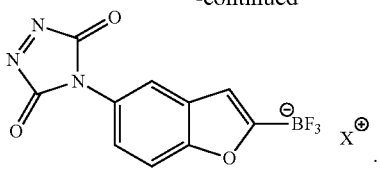

Organo-bis-trifluoroborate can also be designed for negative ion mass-spectrometric application having structural formula AII.

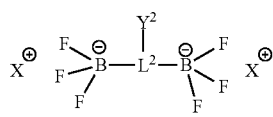

(AII)

wherein $Y^2$ is a functional group selected from the group consisting of an alcohol, alkoxy, aryloxy, diene, dienophile, carboxylic acid, amine, thiol, alkyl halide, ketone, aldehyde, aminooxy, hydrazine and its derivatives, activated ester, acid halide, isocyanate or thio-isocyanate, azo, alkyne, 1,3-dipolariphile, sulfonyl chloride, glyoxal, epoxide or oxirane, carbonate, aryl halide such as fluorobenzene derivatives, imidoester or imidate, anhydride, fluorophenyl ester, hydroxymethyl phosphine derivative, maleimide, aziridine, acryloyl derivative, arylating agent such as derivatives of benzene that possess either halogen or sulfonate groups on the ring, thiol-disulfide exchange reagent such as pyridyldithiol and thiolnitrobenzoic acid, or vinylsulfone group;

$L^2$ is a linker or a combination of 2 to 4 linkers that independently selected from the group consisting of $C_1$-$C_{20}$ alkyl, —$(CH_2CH_2O)_{1-36}$—, —$(CH_2CH_2O)_{1-36}$—$CH_2$—, a peptide, a peptidomimetic oligomer, alicyclyl, optionally substituted alicyclyl, heteroalicyclyl, optionally substituted heteroalicyclyl, optionally substituted aryl.

$X^\oplus$ is any positively charged counter ion.

$Y^1$ of the bis-organo-trifluoroborate compound of the general formula AII can be an aldehyde and ketone reactive aminooxy (—$ONH_2$) group. In some cases, the bis-organo-trifluoroborate compound of the general formula AII has a specific chemical structure (AIII).

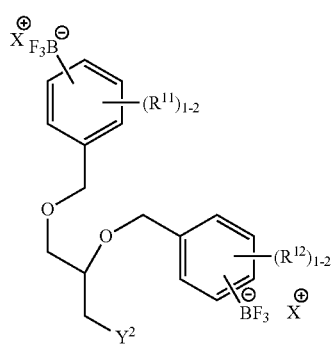

(AIII)

wherein $R^{11}$ and $R^{12}$ is independently selected from a group consisting H and alkoxy.

The synthetic route to prepare compounds of formula AIII has been disclosed herein using two compounds one including an aminooxy (—$ONH_2$) and another acid reactive amine group (Example 7 & 8).

Synthetic route to other organo-bis-trifluoroborate compound of general formula AII has also been disclosed herein (Example 6):

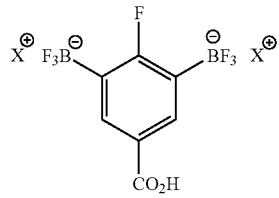

In some cases, the union of "reactive group-linker-organo-bis-trifluoroborate" or "reactive group-linker-organo-trifluoroborate" can be designed as a family of isobaric sets of mass tags or reagents to be used in negative ion mode. In such a family, a combination of heavy stable isotopes, including but not limited to $^{10}B$ and $^{11}B$, $^{12}C$ and $^{13}C$, $^{14}N$ and $^{15}N$, $^{16}O$ and $^{18}O$, or $^{1}H$ and $^{2}H$ isotopes, are used such that the total additional mass is distributed between the reactive group, linker, and trifluoroborate moiety. In such a case a set of isobaric multiplexing reagents can be generated for parallel or simultaneous analysis.

In some cases, the union of "reactive group-linker-organo-bis-trifluoroborate" or "reactive group-linker-organo-trifluoroborate" can be designed as a family of mass differential sets of mass tags or reagents to be used in negative ion mode. In such a family, a combination of heavy stable isotopes, including but not limited to $^{10}B$ and $^{11}B$, $^{12}C$ and $^{13}C$, $^{14}N$ and $^{15}N$, $^{16}O$ and $^{18}O$, or $^{1}H$ and $^{2}H$ isotopes, are used such that the additional mass is distributed between the reactive group, linker, and trifluoroborate moiety. In such a case a set of mass differential multiplexing reagents can be generated for parallel or simultaneous analysis.

In some embodiments of an analyte tagged with the organo-trifluoroborate or organo-bis-trifluoroborate mass tags, the fragmentation pattern of the combined molecule is dependent on the analyte, linker, and tag's property or a combination of all. Each tagged analyte has to be optimized for fragmentation in negative ion mode so that a suitable transition or transitions can be used to detect that specific analyte in a biological, natural, or environmental matrix. An enhanced detection limit is the essence of finding such an optimal transition.

In addition to the need for a high-resolution instrument, calibration standards over a wide span of molecular weights are needed to achieve identification of analytes by accurate mass determination. Formulation of a calibration standard for negative ion mode is still a challenge because of the limited availability of negatively charged molecules with similar ionization propensities but available in a broad range of molecular weight. Organo-trifluoroborates can be used as negative ion mass calibrators. A molecular weight ladder of organo-trifluoroborate in specific formulation can be used as a calibration mix. The molecular weight ladder can be easily assembled by conjugation of the organo-trifluoroborate mass tag with the same class of molecules, such as discrete polyethylene glycol (dPEG) (Example 9, FIGS. 11 & 12).

Sample preparation is an integral part of analyte estimation. In some cases the sample are processed to enrich the analyte present in the sample. Sample processing can be done using various methods, including but not limited to, protein precipitation by organic solvent, solid phase extraction, liquid-liquid extraction, solid liquid extraction, ultracentrifugation, protein removal by molecular weight cut-off membranes, protein removal by filtration through hollow fiber, gel electrophoresis, and purification by various medias such as silica gel, Celite®, reversed phase silica, or hydrophilic silica. Analytes in the samples can be enriched or purified by affinity purification. Non-limiting examples include antibody, chelators, affinity tags, and reversible binders/releasers. After sample preparation, further reduction of the volume of the prepared sample may be necessary to increase the effective concentration of the analyte. Labeling of the analyte in the sample by organo-trifluoroborate reagents can be done before or after sample preparation depending on the nature of the analytes and nature of the tagging reaction. Internal standard may be added to the samples at any stage but is preferable at an early stage of sample preparation.

In some cases a set of calibrators are prepared using known concentrations of analytes and its labeled internal standard (IS). Labels in IS can be of many types. In some embodiments labeled IS will be deuterated ($^2$H) analytes. In some other embodiments, labeled IS is independently $^{13}$C or $^{15}$N enriched analytes. In some embodiments, labeled IS is a combination of all the above. In some embodiments, such calibrators are spiked into analyte-depleted samples to generate a set of calibrators. Such calibrators are used to generate a calibration curve, which includes concentration vs. mass spectrometric response factors. The concentration of the analyte in unknown samples can be determined from the calibration curve.

Internal standard may be the same analyte labeled with a heavy atom or another molecule of similar chemical and physical properties.

Standards are added to the analyte to assist in accurate quantitation and may be either an internal or external standard.

In some embodiments, an artificial analyte-depleted matrix or sample can be generated by dissolving standard highly abundant proteins such as bovine serum albumin (BSA) or human serum albumin (HSA) in aqueous buffers.

In some embodiments, the processed samples including analytes and IS are reacted with organo-trifluoroborate reagents and analyzed by LC-MS/MS analysis.

The foregoing aspects and embodiments of the invention may be more fully understood by referencing the following figures, detailed description, and claims.

EXAMPLES

The following examples contain important additional information, exemplification, and guidance that can be adapted to the practice of this invention in its various embodiments and equivalents thereof. Practice of the invention will be more fully understood from the following examples, which are presented here for illustrative purposes only and should not be construed as limiting in anyway.

Instrumentation:

$^1$H-NMR spectra were recorded at 500 MHz (Brukar) and are reported in parts per million (ppm) on the δ scale relative to residual CHCl$_3$ (δ 7.25) and DMSO-d6 (δ 2.49). HPLC was performed in an Agilent 1100 HPLC system with automatic sample injector and diode array detector. Analytical HPLC was performed on an XTerra™ RP$_{18}$ column (Waters, 5 μm, 4.6×250 mm). The HPLC method used (method A) was a linear gradient of AB solvent (2% B to 98% B in 15 minutes) at a flow rate of 1 mL/min. Solvent A was water and solvent B was acetonitrile. The UV detector was set at 210 nm and 254 nm. Most mass spectra were collected on a Quadrupole MDS Sciex Q-TRAP.

Solvents and Reagents:

All moisture-sensitive reactions were performed in an inert, dry atmosphere of nitrogen. Reagent grade solvents were used for chromatography and extraction. Potassium (boromethyl)trifuoroborate were purchased from TCI America. Anhydrous tetrahydrofuran (THF), anhydrous dimethyl formamide (DMF), potassium tert-butoxide (1M in THF solution), trifluoroacetic acid, di-tert-butyl dicarbonate, di-tert-butyl dicarbonate (Boc$_2$O), sodium hydride (60% dispersion in oil), benzofuran-2-trifluoroborate, potassium trans-stryltrifluoroborate were purchased from Sigma-Aldrich. m-dPEG®$_7$-alcohol, m-dPEG®$_4$-alcohol, m-dPEG®$_{15}$-alcohol, and m-dPEG®$_{23}$-alcohol were purchased from Quanta Biodesign (dPEG® is a trademark of Quanta Biodesign); H$_2$NO—(CH$_2$)$_3$—OH was purchased from HuHuTechnology (San Diego, Calif.); and ACS grade solvents were purchased from EMD or BDH. All other chemicals and reagents were purchased from Alfa Aesar and used as received.

Chromatography:

Thin-layer chromatography (TLC) analysis was performed using EMD TLC silica gel 60 F254 (0.25 mm thickness). The plates were visualized first with UV illumination, followed by charring with Verghn's reagent (ceric ammonium molybdate, 2.5% ammonium molybdate, 1% cerium sulfate in 10% aqueous sulfuric acid). Flash chromatography was performed on an ISCO companion using pre-packed columns. The solvent compositions were on a volume/volume (v/v) basis.

Example 1-2

Synthesis of Aldehyde and Ketone Reactive Trifluoroborate Mass Tags

Example 1

Synthesis of Mass Differential Aldehyde and Ketone Reactive Mass Tags

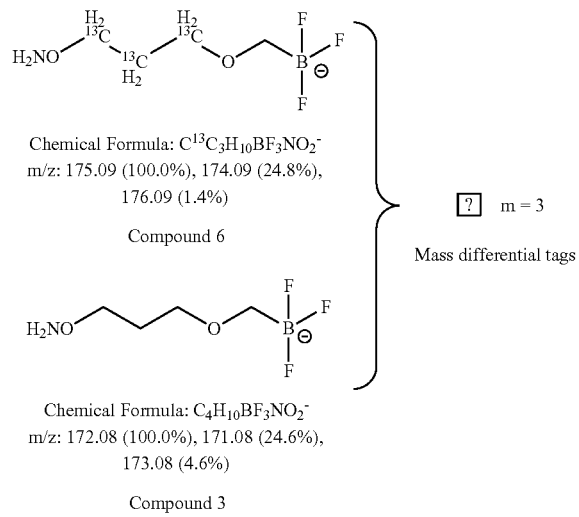

Compound 1 (BocNHO—(CH$_2$)$_3$—OH):

Di-tert-butyl dicarbonate (2.61 g, 12 mmol) was added to a stirred solution of H$_2$NO—(CH$_2$)$_3$—OH (1 g, 10.98 mmol) in THF at room temperature (RT). The reaction was then stirred for an additional 16 hr. Next, the reaction mixture was concentrated in vacuo and the residue was purified by silica gel chromatography (ethyl acetate:hexanes=6:1) to obtain 1.8 g of compound 1 (86%) as a colorless solid of low melting point.

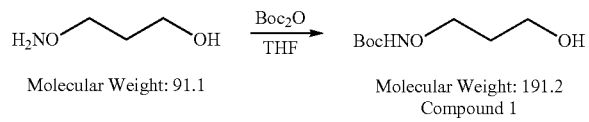

Compound 2 ([BocNHO—(CH$_2$)$_3$—OCH$_2$—BF$_3$]$^-$K$^+$):

The compound was synthesized by following similar procedure from the literature (WO2013/092791A1). To a well stirred THF (anhydrous) suspension of NaH (25 mg, 0.11 mmol; 60% dispersion in oil) in round bottom flask under argon atmosphere, BocNHO—(CH$_2$)$_3$—OH (108 mg, 0.1 mmol) was added as THF (anhydrous) solution over a period of 2 min using a gas tight syringe at 0° C. The reaction was warmed to RT for 30 minutes then cooled again at 0° C. A solution of Potassium (bromomethyl)trifluoroborate (259 mg, 0.129 mmol) in anhydrous THF was added to the reaction mixture and stirred for 18 h at RT (monitoring by HPLC). Excess THF was removed in vacuo. The residue was suspended in a minimum amount of acetone and transferred to a 15 mL centrifuge tube. Diethyl ether was added and a white solid was precipitated out. The precipitated solid was separated from the diethyl ether and washed 3 times with diethyl ether by centrifugation. The white solid obtained was dried in vacuo to yield 177.9 mg of the crude product. The crude product was dissolved in water and subjected to the LC-MS analysis without further purification.

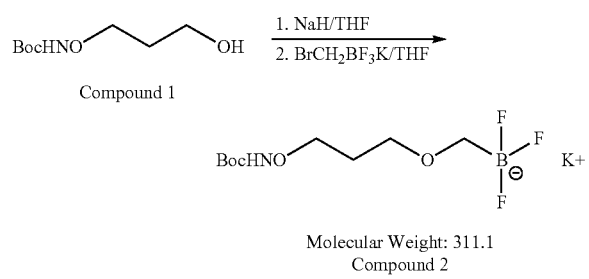

Alternative Method to Synthesize Compound 2:

To a well stirred THF (anhydrous) solution of BocNHO—(CH$_2$)$_3$—OH (50.7 mg, 0.15 mmol) in round bottom flask under argon atmosphere, 180 μL of 1M tBuOK in THF solution (0.18 mmol) was added over a period of 2 min using a gas tight syringe at 0° C. The reaction was warmed to RT for 30 minutes. A solution of potassium (bromomethyl)trifluoroborate (20 mg, 0.1 mmol, 0.1 mM solution) in anhydrous THF/DMF (v/v: 1:1) was added to the reaction mixture and stirred for 18 h at RT (monitoring by HPLC). The residue was transferred to a 15 mL centrifuge tube. Diethyl ether was added and a white solid was precipitated out. The precipitated solid was separated from the diethyl ether and washed 3 times with diethyl ether by centrifugation. The white solid obtained was dried in vacuo to yield 64 mg of the crude product. The crude product was dissolved in water and subjected to the LC-MS analysis without further purification.

MS and MS/MS Analysis:

In negative ion MS mode, compound 2 ([BocNHO—(CH$_2$)$_3$—OCH$_2$—BF$_3$]$^-$K$^+$) showed distinct natural isotopic pattern expected for the anion [BocNHO—(CH$_2$)$_3$—OCH$_2$—BF$_3$]$^-$: major isotopic pattern m/z=271.1 (M$^-$ with $^{10}$B, approximately 20%) and m/z=272.1 (M$^-$ with $^{11}$B isotope, approximately 79%). In MS/MS mode, fragmentation of the major isotopic ion at m/z=272.1 with increasing collisional energy (CE scan) following fragments ions are observed (e.g., FIGS. 13 & 14).

a) m/z=252.2 which corresponds to the following structure after neutral loss HF molecule as anticipated.

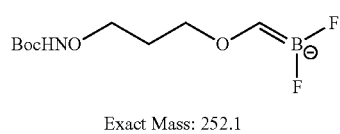

Exact Mass: 252.1 b) m/z=152.0 which corresponds to the following structure after further loss of Boc group.

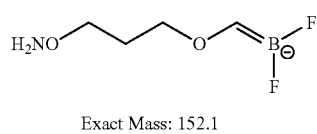

Exact Mass: 152.1 c) m/z=136.9 which corresponds to the following structure after further loss of NH$_2$ group.

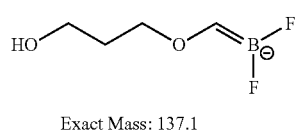

Exact Mass: 137.1

Compound 3 ([TFA.NH$_2$O—(CH$_2$)$_3$—OCH$_2$—BF$_3$]$^-$K$^+$):
[BocNHO—(CH$_2$)$_3$—OCH$_2$—BF$_3$]$^-$K$^+$ (100 mg) is treated with 80% of aqueous trifluoroacetic acid (1 mL) for 15 min and then dried under vacuum to generate the unprotected aminooxy compound.

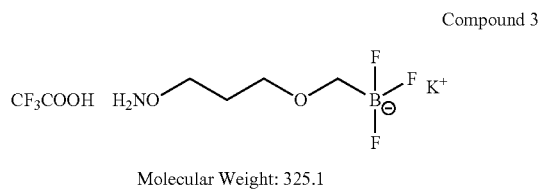

Compound 4 (N-hydroxyphthalimide-$^{13}$C$_3$-propyl alcohol):

1,8-diazabicycloundec-7-ene (DBU) (0.69 mL, 4.57 mmol) is added to a THF solution of N-hydroxyphthalimide (750 mg, 4.57 mmol, 5 mL) and stirred at RT for 1 h. The reaction mixture is then added to a THF solution of 3-bromo-1-propanol-$^{13}$C$_3$ (0.375 mL, 4.15 mmol, 5 mL, Aldrich 642525) in a round-bottom flask over the course of 5 minutes at RT. The resulting solution is stirred for another 4 hours. The solvent is removed in vacuo and the residue is partitioned between 0.25M HCl (150 mL) and ethyl acetate (350 mL). Ethyl acetate layer is washed with brine, dried over anhydrous sodium sulfate, filtered and concentrated in vacuo. The resulting residue is then purified by a silica gel chromatography (ethyl acetate: hexanes=6:1) to obtain compound 4 as while solid. The identity of the product is confirmed by NMR and MS.

Compound 6 ([TFA.NH$_2$O—($^{13}$CH$_2$)$_3$—OCH$_2$—BF$_3$]$^-$K$^+$):

A solution of hydrazine in THF (4 mL, 1 M) is added under argon atmosphere to a solution of N-hydroxyphthalimide-$^{13}$C$_3$-propyl alcohol (560 mg, 2.5 mmol) in THF (5 mL). The reaction mixture is stirred at RT for 3 h. A white solid is precipitated out. The precipitate is removed by filtration. The filtrate is dried over anhydrous Na$_2$SO$_4$, filtered, and concentrated under reduced pressure to obtain compound 5 (H$_2$NO—($^{13}$CH$_2$)$_3$—OH) as an oil. This product is then converted to the mass differential mass-tag analog compound 6 ([TFA.NH$_2$O—($^{13}$CH$_2$)$_3$—OCH$_2$—BF$_3$]$^-$K$^+$) following the same protocol as describes for compound 2 & 3.

mmol, 5 mL) over the course of 5 minutes at RT. The resulting solution is stirred for another 4 hours. The solvent is removed in vacuo and the residue is partitioned between 0.25M HCl (150 mL) and ethyl acetate (350 mL). Ethyl acetate layer is washed with brine, dried over anhydrous sodium sulfate, filtered and concentrated in vacuo. The resulting residue is then purified by a silica gel chromatography (ethyl acetate: hexanes=6:1) to obtain compound 7 as a while solid. The identity of the product is confirmed by NMR and MS.

Compound 9 (5-(2-Boc-aminoxy-ethyl)-2,3-dihydrobenzofuran):

A solution of hydrazine in THF (4 mL, 1 M) is added under argon atmosphere to a solution of 5-(2-N-hydroxyphthalimide-ethyl)-2,3-dihydrobenzofuran (750 mg, 2.44 mmol) in THF (5 mL). The reaction mixture is stirred at RT for 3 h. A white solid is precipitated out. The precipitate is removed by filtration. The filtrate is dried over anhydrous Na$_2$SO$_4$, filtered, and concentrated under reduced pressure to obtain an oil. The oil is then treated with Boc$_2$O (638 mg, 2.92 mmol) in THF (5 mL) and allowed to react for overnight at RT. The solvent is then removed in vacuo and Boc protected 5-(2-aminoxy-ethyl)-2,3-dihydrobenzofuran is purified by silica gel chromatography (Ethylacetate:hexanes=3:1) to obtain a white solid. The identity of the product is confirmed by NMR and MS.

Compound 10:

compound 9 is then converted to the 2-trifluoroborate derivative (compound 10) following a literature procedure for a similar compound (Journal of Organic Chemistry, 60(10), 3028-34; 1995).

Compound 11:

Boc protecting group is then removed from 5-(2-Boc-aminoxy-ethyl)-2,3-dihydrobenzofuran by treatment with TFA-water for 15 minutes to produce compound 11 (5-(2-aminoxy-ethyl)-2,3-dihydrobenzofuran TFA salt) as an oil. The identity of the product is confirmed by MS.

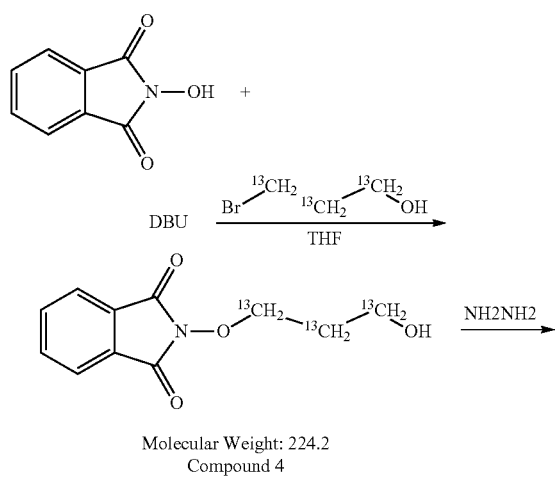

Example 2

Synthesis of Benzofuran Based Aldehyde and Ketone Reactive Mass Tags

Compound 7 (5-(2-N-hydroxyphthalimide-ethyl)-2,3-dihydrobenzofuran):

5-(2-bromoethyl)-2,3-dihydrobenzofuran is synthesize by following a literature procedure (Zhongguo Yiyao Gongye Zazhi, 43(4), 254-255; 2012). To a THF solution of N-hydroxyphthalimide (678 mg, 4.15 mmol, 5 mL) is added DBU (0.63 mL, 4.15 mmol). The reaction mixture is stirred at RT for 1 h. This solution is then added to a THF solution of 5-(2-bromoethyl)-2,3-dihydrobenzofuran (780 mg, 3.46

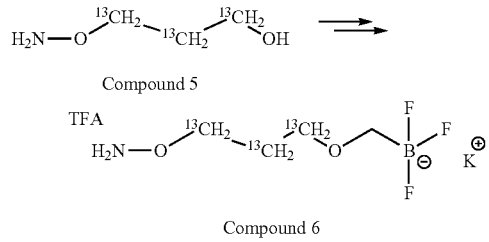

-continued

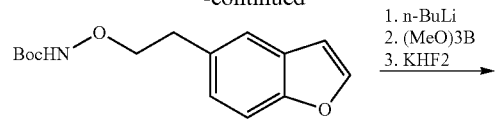

Molecular Weight: 277.3
Compound 9

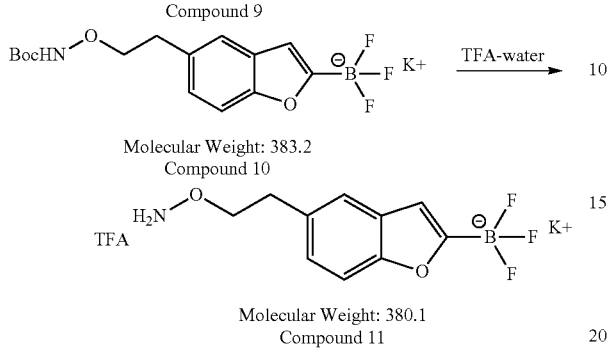

Molecular Weight: 383.2
Compound 10

Molecular Weight: 380.1
Compound 11

Example 3

Synthesis of Amine Reactive Trifluoroborate Mass Tag

Compound 12:

To a solution of potassium 4-carboxyphenyltrifluoroborate (228 mg, 1 mmol, Sigma-Aldrich, 657069) in anhydrous THF (5 mL) is added a solution of N-trifluoroacetoxy succinimide (211 mg, 1 mmol, NHS-TFA, Tetrahedron Lett. 43, 2002, 7793-7795) in THF (4.5 mL). The reaction mixture is stirred at RT overnight. The solvent is then removed in vacuo and diethyl ether is added. White solid is precipitated out and washed three times with diethyl ether by centrifugation. The residue diethyl ether is removed in vacuo to obtain a white foamy material.

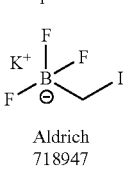

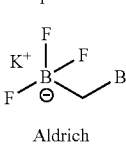

Molecular Weight: 325.1
Compound 12

Example 4

Thiol Reactive Trifluoroborate Mass Tags

The two following commercially available compounds (compound 13 & 14) can be used as thiol reactive mass tags.

Compound 13:

Aldrich
718947

Compound 14:

Aldrich
681342

Example 5

Synthesis of Diene Reactive Trifluoroborate Mass Tag

Compound 17:

4-(1-benzofuran)-1,2,4-triazoline-3,5-dione (compound 15) is synthesized following a literature procedure for a similar compound (Cookson, R. C. et. al. Org. Synth. 1971, 51, 121) using 1-benzofuran-5-yl isocyanate (A ChemTek, 031-5299) and ethyl carbazate. The urazole product (compound 15) is then converted to the 2-trifluoroborate derivative (compound 16) following a literature procedure for a similar compound (Vedejs, E. et. al. Journal of Organic Chemistry, 60(10), 3028-34; 1995). Oxidation of the urazole is performed as described in the literature (Cookson, R. C. Org. Synth. 1971, 51, 121) to obtain compound 17 (the diene reactive trifluoro borate mass tag).

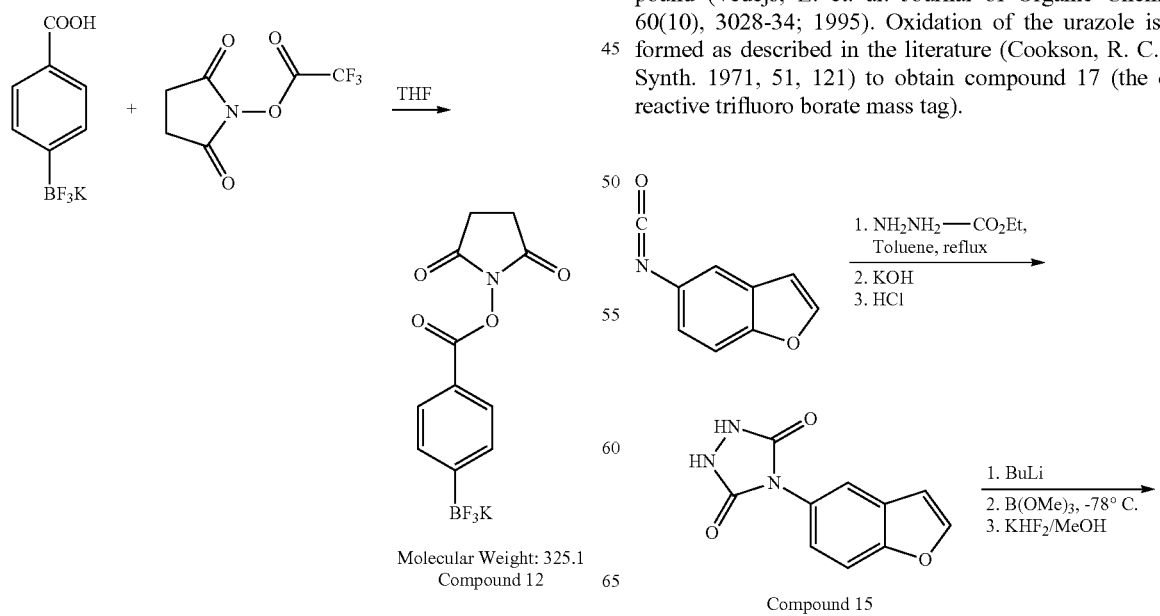

Compound 15

-continued

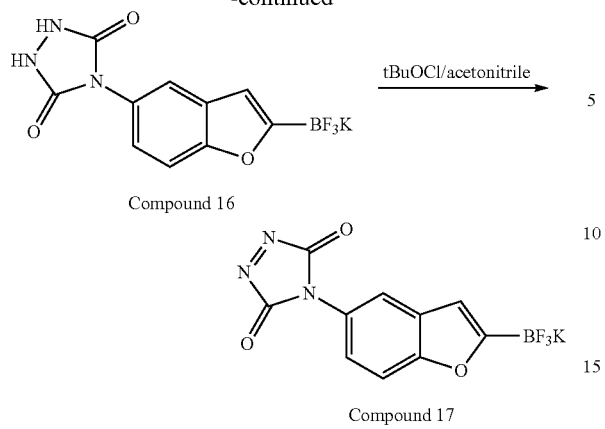

Compound 16

Compound 17

Examples 6, 7 and 8

Synthesis of Bis-Trifluoroborate Mass Tags

Example 6

Amine Reactive Bis-Trifluoroboarate Mass Tag

Compound 19:

A 3 mL of NaOH (1M, 3 mL) solution is added to an acetonitrile solution of methyl 4-fluoro-3,5-bis(4,4,5,5-tetramethyl-1,3,2-dioxaborolan-2-yl)benzoate (375 mg, BoroPharma Inc., Ann Arbor, Mich., 01-0079). After HPLC analysis confirms the completion of the hydrolysis for the starting material, 3 mL of 2M HCl solution is added to neutralize the reaction mixture. Water and excess HCl is then removed in vacuo. The boronic acid (compound 18) is desalted using a C18 cartridge (water wash followed by 50% acetonitrile-water elution). The eluted fractions containing the product are combined and concentrated in vacuo. A solution of $KHF_2$ in water-methanol is then added and the solution is stirred for 3 h. The crude bis-trifluoroborate (compound 19) is purified by a C18 cartridge desalting as described in this section. The identity of the product is confirmed by characteristic MS (m/2-negative ion).

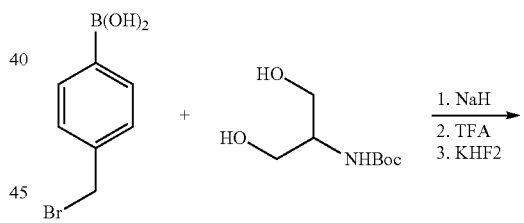

Boronic acid
Compound 18

-continued

Compound 19

Example 7

Acid Reactive Bis-Trifluoroboarate Mass Tag

Compound 20:

A solution of N-Boc-serinol (357 mg, 1.88 mmol, Aldrich, 661074) in THF (5 mL) is added drop wise over 5 minutes to a suspension of NaH (150 mg, 3.75 mmol, 60% dispersion in mineral oil) in anhydrous THF (5 mL). The reaction mixture is stirred at RT for 2 h, then a solution of 4-(bromomethyl) phenylboronic acid (802 mg, 3.75 mmol, Aldrich, 679437) in THF (10 mL) is added. The reaction mixture is stirred for another 10 hrs. The solvent is then removed in vacuo, and 5 mL of ice cold 80% TFA in water is added to the residue slowly. After stirring at RT for 15 minutes, the reaction mixture is neutralized with 1M NaOH solution, treated with a solution of $KHF_2$ in water-methanol, and then stirred for another hour. Purification of the product is achieved by a C18 column (acetonitrile-water). The identity of the product is confirmed by MS and NMR.

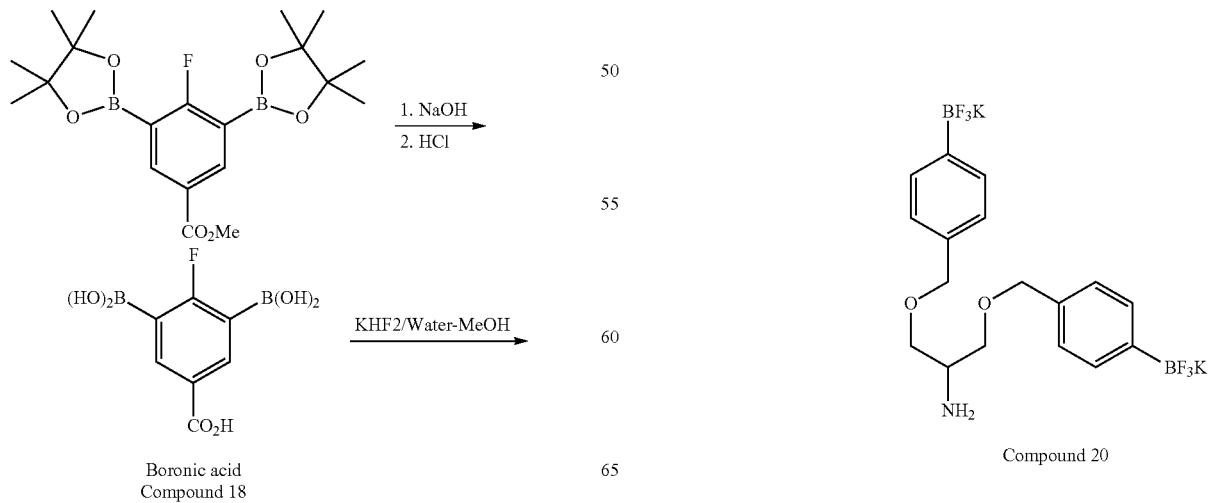

Compound 20

Example 8

Aldehyde and Ketone Reactive Bis-Trifluoroboarate Mass Tag

Compound 21 (3-(Boc-aminooxy)-1,2-propanediol):

Compound 21 is synthesized by treating O-(2,2-Dimethyl-[1,3]dioxolan-4-ylmethyl)-hydroxylamine (350 mg, 2.38 mmol, HuHu Technology, HH200-202) with 5 M HCl (5 mL) solution for one hour followed by the basification with saturated $NaHCO_3$. A solution of $Boc_2O$ (625 mg, 1.54 mmol) in THF (5 mL) is then added to the reaction mixture, and stirred at RT for 11 hrs. The reaction mixture is extracted three times with ethyl acetate. The combined organic layers are washed with brine, dried over anhydrous $Na_2SO_4$, filtered, and concentrated in vacuo. The oily residue is purified by silica gel chromatography to obtain the desired product (ethylacetate:hexanes=65:25). The identity of the product is confirmed by MS and NMR.

Compound 22 (aminoxy-bis-trifluoroborate):

Compound 22 is synthesized from 4-(bromomethyl)phenylboronic acid and 3-(boc-aminooxy)-1,2-propanediol following similar synthetic route as described for compound 20.

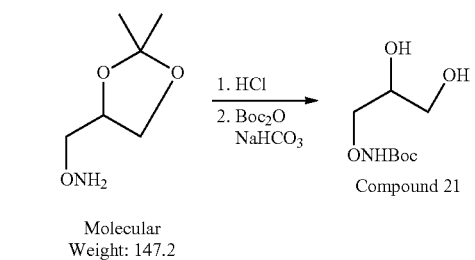

Compound 21
Molecular Weight: 147.2

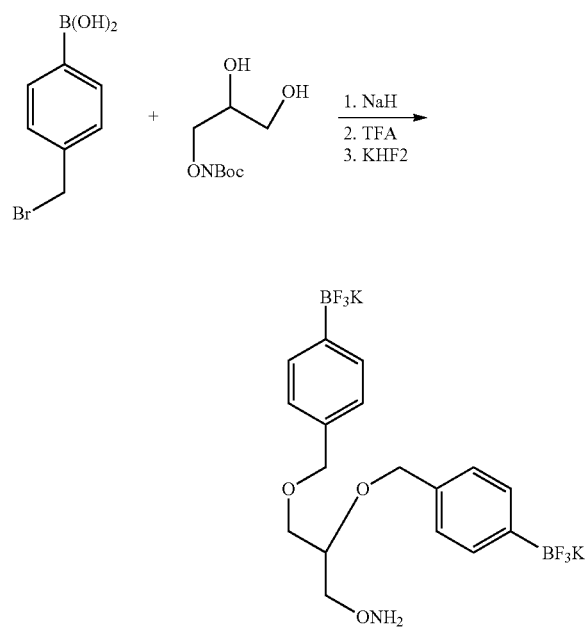

Compound 22

Example 9

Synthesis of Discrete Polyethyleneglycol (dPEG) Based Negative Mode Mass Calibrators (MW Ladder)

Compound 23 and Compound 24:

To a well stirred THF (anhydrous) solution of m-dPEG®$_4$-alcohol (12.5 mg, 0.06 mmol) and dPEG®$_7$-alcohol (33.4 mg, 0.098 mmol) in round bottom flask under argon atmosphere, 190 μL of 1M tBuOK in THF solution (0.19 mmol) was added over a period of 2 min using a gas tight syringe at 0° C. The reaction was warmed to RT for 30 minutes. A solution of potassium (bromomethyl)trifluoroborate (21.1 mg, 0.105 mmol, 0.1 mM solution) in anhydrous THF/DMF (v/v: 1:1) was added to the reaction mixture and stirred for 16 h at RT (monitoring by HPLC). The residue was transferred to a 15 mL centrifuge tube. Diethyl ether was added and a white solid was precipitated out. The precipitated solid was separated from the diethyl ether and washed 3 times with diethyl ether by centrifugation. The white solid obtained was dried in vacuo to yield 31 mg of the crude product. The crude product was dissolved in water/MeOH (v/v: 1:1) and subjected to the LC-MS analysis without further purification.

Compound 25:

To a well stirred THF (anhydrous) solution of m-dPEG®$_{15}$-alcohol (41.6 mg, 0.06 mmol) in round bottom flask under argon atmosphere, 72 μL of 1M tBuOK in THF solution (0.072 mmol) was added over a period of 2 min using a gas tight syringe at 0° C. The reaction was warmed to RT for 30 minutes. A solution of potassium (bromomethyl)trifluoroborate (10 mg, 0.05 mmol, 0.1 mM solution) in anhydrous THF/DMF (v/v: 1:1) was added to the reaction mixture and stirred for 16 h at RT (monitoring by HPLC). The residue was transferred to a 15 mL centrifuge tube. Diethyl ether was added and a white solid was precipitated out. The precipitated solid was separated from the diethyl ether and washed 3 times with diethyl ether by centrifugation. The white solid obtained was dried in vacuo to yield 18.6 mg of the crude product (45.8%). The crude product was dissolved in water and subjected to the LC-MS analysis without further purification.

Compound 26:

To a well stirred THF (anhydrous) solution of m-dPEG®$_{23}$-alcohol (36.4 mg, 0.035 mmol) in round bottom flask under argon atmosphere, 36 μL of 1M tBuOK in THF solution (0.036 mmol) was added over a period of 2 min using a gas tight syringe at 0° C. The reaction was warmed to RT for 30 minutes. A solution of potassium (bromomethyl)trifluoroborate (5 mg, 0.025 mmol, 0.1 mM solution) in anhydrous THF/DMF (v/v: 1:1) was added to the reaction mixture and stirred for 16 h at RT (monitoring by HPLC). The residue was transferred to a 15 mL centrifuge tube. Diethyl ether was added and a white solid was precipitated out. The precipitated solid was separated from the diethyl ether and washed 3 times with diethyl ether by centrifugation. The white solid obtained was dried in vacuo to yield 27.8 mg of the crude product (95.5%). The crude product was dissolved in water/MeOH (v/v: 1:1) and subjected to the LC-MS analysis without further purification.

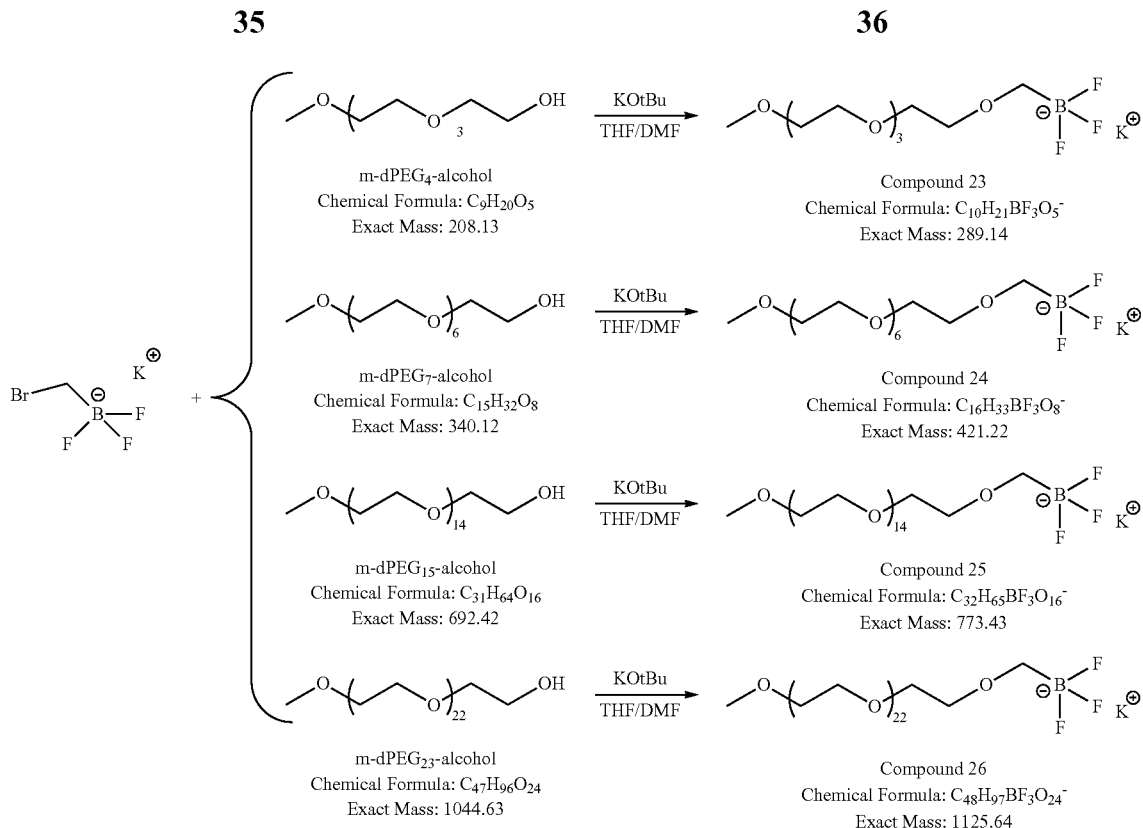

Example 10

Application of Ketone-Reactive Trifluoroborate Mass Tags for Labeling and Analysis of Ketone Analyte A solution of ketone reactive trifluoroborate mass tag such as a trifluoroborate aminooxy compound (compound 11 is used here as an example) in methanol (1 mg/ml) is mixed with a trace amount of ketone analyte such as testosterone (1 μg) and acetic acid (5% final concentration). After mixing at RT for one hour, the reaction mixture is submitted directly for LC-MS/MS analysis. The predicted mass and fragmentation pattern of the tagged analyte are shown in FIG. 8.

Example 11

Application of Amine-Reactive Trifluoroborate Mass Tags for Labeling and Analysis of Amine Analyte A solution of an amine reactive trifluoroborate mass tag such as a trifluoroborate NHS ester (compound 12 is used here as an example) in acetonitrile (1 mg/ml) is mixed with a trace amount of amine analyte such as catecholamine (1 μg) and 10 μl of triethylamine bicarnoate buffer. After mixing at RT for one hour, the reaction mixture is submitted directly for LC-MS/MS analysis. The predicted mass and fragmentation pattern of the tagged analyte are shown in FIG. 9.

Example 12

Application of Ketone-Reactive Mass-Differential Trifluoroborate Mass Tags for Labeling and Analysis of Ketone Analyte A solution of ketone-reactive mass-differential trifluoroborate mass tag such as compound 11 in methanol (1 mg/ml) is mixed with a trace amount of ketone analyte such as testosterone (1 μg, sample 1) and acetic acid (5% final concentration) at RT for one hour. In a separate vial, a solution of isotopic analog of compound 11 (compound 27) in methanol (1 mg/ml) is mixed with another testosterone sample (sample 2) and acetic acid (5% final concentration) at RT for one hour. After derivatization with the mass tags, the two samples are mixed and are submitted directly for LC-MS/MS analysis. The predicted mass and fragmentation pattern of the tagged analytes are shown in FIG. 10. Because of the difference in the mass of parent-daughter ions, multiple samples can be analyzed in one LC-MS/MS run, increasing the throughput of analysis.

Example 13

Predictable Fragmentation of Organo-Trifluoroborates

Two organo-trifluoroborate molecules (benzofuran-2-trifluoroborate and potassium trans-styryltrifluoroborate) were dissolved in methanol-water and directly infused into a triple quadrupole mass spectrometer. Parent ions were detected as negative ions and then the molecules fragmented with increasing amounts of collision energy (CE scan). As shown in FIG. 2, FIG. 3, and FIG. 4, two organo-trifluoroborate molecules were fragmented with an increasing amount of collisional energy. Potassium benzofuran-2-trifluoroborate, which was detected as a negative ion at 185.00 amu, lost a $BF_3$ molecule at a collisional energy of −45 ev, producing the benzofuran anion, which was detected at 116.99 amu. Potassium trans-styryltrifluoroborate, which was detected as a negative ion of molecular weight 171.04 underwent successive fragmentations with increasing collisional energy. At around −15 ev, a molecule of hydrogen fluoride is lost, producing daughter ion 1 of molecular weight 151.08. At a higher collisional energy, loss of HF and other significant neutral losses were observed (FIG. 4). The fragmentation process is so spontaneous that even a benzyl carbanion was observed (m/z=77.07).

The above example support that organo-trifluoroborates can be fragmented in a predictable way, generating different product ions at different collisional energies. The fragmentation pathway produced only a few ions, unlike positive mode fragmentation in which a plethora of ions are generally observed by indiscriminate fragmentation of the molecule. Overabundance of ions in positive mode reduces the amount of ion current to specific ions, reducing the overall sensitivity of the specific transition and resulting in low sensitivity for the assay. However, the production of fewer specific ions in negative mode ensures the allocation of a majority of the ion current in one transition. This funneling of ion current enables a highly sensitive assay.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

What is claimed is:

1. A method for mass spectrometric analysis, comprising fragmenting organo-trifluoroborate or an analyte tagged with one or more organo-trifluoroborate mass tags comprising one or more trifluoroborate groups in negative ion mode to produce one or more negatively charged fragment ions and one or more molecules with no charge.

2. The method of claim 1, wherein the mass spectrometric analysis provides qualitative monitoring and/or analysis of the analyte.

3. The method of claim 1, wherein the mass spectrometric analysis provides quantitative monitoring and/or analysis of the analyte.

4. The method of claim 1, wherein the fragmentation energy is zero.

5. The method of claim 1, wherein one or more of the organo-trifluoroborate mass tags has structural formula:

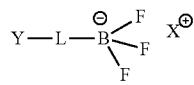

wherein

Y is a reactive group selected from the group consisting of an alcohol, alkoxy, aryloxy, diene, dienophile, carboxylic acid, amine, thiol, alkyl halide, ketone, aldehyde, aminooxy, hydrazine and its derivatives, activated ester, acid halide, isocyanate or thio-isocyanate, azo, alkyne, 1,3-dipolariphile, sulfonyl chloride, glyoxal, epoxide or oxirane, carbonate, aryl halide such as fluorobenzene derivatives, imidoester or imidate, anhydride, fluorophenyl ester, hydroxymethyl phosphine derivative, maleimide, aziridine, acryloyl derivative, arylating agent such as derivatives of benzene that possess either halogen or sulfonate groups on the ring, thiol-disulfide exchange reagent such as pyridyldithiol and thiolnitrobenzoic acid, or vinylsulfone group; and L is a bond or a linker; and $X^{\oplus}$ is a positively charged counter ion.

6. The method of claim 5, wherein one or more of the organo-trifluoroborate mass tags is labeled with one or more stable heavy isotopes selected from $^{10}B$, $^{11}B$, $^{12}C$, $^{13}C$, $^{14}N$, $^{15}N$, $^{16}O$, $^{18}O$, $^{1}H$ and $^{2}H$ isotopes at select atomic sites such that the total additional mass due to heavy isotope labeling is distributed between the reactive group, the linker, and trifluoroborate group to produce a set of isobaric and mass differential tags.

7. The method of claim 1, wherein one or more of the organo-trifluoroborate mass tags comprise two or more trifluoroborate groups, which organo-trifluoroborate mass tags undergo fragmentation(s) in negative ion mode to produce one or more fragment ions that are mono-negative or multi-negative, structure-specific daughter ions.

8. The method of claim 7, wherein one or more of the organo-trifluoroborate mass tags comprise bis-trifluoroborate groups.

9. The method of claim 8, wherein one or more of the organo-trifluoroborate mass tags has structural formula:

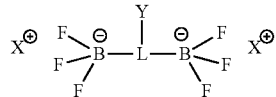

wherein

Y is a reactive group selected from the group consisting of an alcohol, alkoxy, aryloxy, diene, dienophile, carboxylic acid, amine, thiol, alkyl halide, ketone, aldehyde, aminooxy, hydrazine and its derivatives, activated ester, acid halide, isocyanate or thio-isocyanate, azo, alkyne, 1,3-dipolariphile, sulfonyl chloride, glyoxal, epoxide or oxirane, carbonate, aryl halide such as fluorobenzene derivatives, imidoester or imidate, anhydride, fluorophenyl ester, hydroxymethyl phosphine derivative, maleimide, aziridine, acryloyl derivative, arylating agent such as derivatives of benzene that possess either halogen or sulfonate groups on the ring, thiol-disulfide exchange reagent such as pyridyldithiol and thiolnitrobenzoic acid, or vinylsulfone group;

L is a bond or a linker; and $X^\oplus$ is a positively charged counter ion.

10. The method of claim 9, wherein one or more of the organo-trifluoroborate mass tag is labeled with one or more stable heavy isotopes selected from $^{10}B$ and $^{11}B$, $^{12}C$ and $^{13}C$, $^{14}N$ and $^{15}N$, $^{16}O$ and $^{18}O$, $^{1}H$ and $^{2}H$ isotopes at select atomic sites such that the total additional mass due to heavy isotope labeling is distributed between the reactive group, the linker, and trifluoroborate moiety to produce a set of isobaric and mass differential tags.

11. The method of claim 1, wherein a mixture of the organo-trifluoroborate mass tags is used for calibration of mass spectrometer in negative ion mode.

12. The method of claim 11, wherein a mixture of the organo-trifluoroborate mass tags is used for calibration of mass spectrometer in high resolution mass (HRMS) negative ion mode with >15,000 resolving power (R>15,000).

13. The method of claim 11, wherein a mixture of the organo-trifluoroborate mass tags is used for calibration of mass spectrometer in accurate mass negative ion mode.

14. The method of any of claims 11, 12, and 13, wherein the mixture of the organo-trifluoroborate mass tags comprises enriched $^{10}B$ or $^{11}B$ isotope.

15. The method of any of claims 5 and 9, wherein $X^\oplus$ is selected from the group consisting of K$^+$, Cs$^+$, Rb$^+$, quaternary ammonium, pyridinium, pyrazolium, thiazolium, morpholium, triazolium, imidazolium, bezoxazolium, thiadiazolium, oxadiazolium and guanidinium ions.

16. The method of claim 15, wherein $X^\oplus$ is K$^+$.

17. The method of claim 1, further comprising
detecting one or more negatively charged fragment ions.

18. An organo-trifluoroborate compound having structural formula:

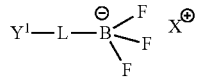

wherein
Y$^1$ is a reactive group selected from the group consisting of alcohol, alkoxy, a diene, dienophile, aminooxy, activated ester, N-hydroxysuccinimide ester, alkyl halide, aryl halide, maleimide, thiol-disulfide exchange reagent such as pyridyldithiol and thiolnitrobenzoic acid, or vinylsulfone group;

L$^1$ is a linker or a combination of 2 to 4 linkers that are individually selected from the group consisting of C$_1$-C$_{20}$ alkyl, —(CH$_2$CH$_2$O)$_{1-36}$—, —(CH$_2$CH$_2$O)$_{1-36}$—CH$_2$—, a peptide, a peptidomimetic oligomer, alicyclyl, optionally substituted alicyclyl, heteroalicyclyl, optionally substituted heteroalicyclyl, and optionally substituted aryl; and $X^\oplus$ is a positively charged counter ion, or

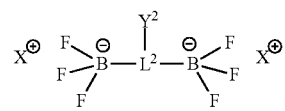

wherein
Y$^2$ is a functional group selected from the group consisting of an alcohol, alkoxy, aryloxy, diene, dienophile, carboxylic acid, amine, thiol, alkyl halide, ketone, aldehyde, aminooxy, hydrazine and its derivatives, activated ester, acid halide, isocyanate or thio-isocyanate, azo, alkyne, 1,3-dipolariphile, sulfonyl chloride, glyoxal, epoxide or oxirane, carbonate, aryl halide such as fluorobenzene derivatives, imidoester or imidate, anhydride, fluorophenyl ester, hydroxymethyl phosphine derivative, maleimide, aziridine, acryloyl derivative, arylating agent such as derivatives of benzene that possess either halogen or sulfonate groups on the ring, thiol-disulfide exchange reagent such as pyridyldithiol and thiolnitrobenzoic acid, or vinylsulfone group;

L$^2$ is a linker or a combination of 2 to 4 linkers that are independently selected from the group consisting of C$_1$-C$_{20}$ alkyl, —(CH$_2$CH$_2$O)$_{1-36}$—, —(CH$_2$CH$_2$O)$_{1-36}$—CH$_2$—, a peptide, a peptidomimetic oligomer, alicyclyl, optionally substituted alicyclyl, heteroalicyclyl, optionally substituted heteroalicyclyl, and optionally substituted aryl; and $X^\oplus$ is any positively charged counter ion.

19. A method for performing an LC-MS analysis, comprising
separating organo-trifluoroborate-tagged analytes by high-pressure liquid chromatography; and
analyzing the separated organo-trifluoroborate tagged analytes by mass spectroscopy in negative ion mode.

20. The method of claim 19, wherein the organo-trifluoroborate comprises organo-multi-trifluoroborate.

* * * * *